(12) United States Patent
Ismael et al.

(10) Patent No.: US 12,193,894 B2
(45) Date of Patent: Jan. 14, 2025

(54) SET OF LAYER-SPECIFIC MOLDING MATRICES

(71) Applicant: EXOCAD GMBH, Darmstadt (DE)

(72) Inventors: Gustavo Ismael, Darmstadt (DE); David Garrubba, Darmstadt (DE)

(73) Assignee: EXOCAD GMBH, Darmstadt (DE)

( * ) Notice: Subject to any disclaimer, the term of this patent is extended or adjusted under 35 U.S.C. 154(b) by 381 days.

(21) Appl. No.: 17/668,449

(22) Filed: Feb. 10, 2022

(65) Prior Publication Data

US 2023/0301758 A1    Sep. 28, 2023

(51) Int. Cl.
| | |
|---|---|
| *A61C 13/00* | (2006.01) |
| *A61C 13/08* | (2006.01) |
| *A61C 13/20* | (2006.01) |
| *A61C 13/34* | (2006.01) |
| *B29C 39/44* | (2006.01) |
| *B29C 64/386* | (2017.01) |
| *B33Y 50/00* | (2015.01) |
| *G05B 19/4099* | (2006.01) |

(52) U.S. Cl.
CPC ...... *A61C 13/0004* (2013.01); *A61C 13/0019* (2013.01); *A61C 13/082* (2013.01); *A61C 13/206* (2013.01); *A61C 13/34* (2013.01); *B29C 39/44* (2013.01); *B29C 64/386* (2017.08); *B33Y 50/00* (2014.12); *G05B 19/4099* (2013.01); *G05B 2219/49023* (2013.01)

(58) Field of Classification Search
CPC ............ A61C 13/0004; A61C 13/0019; A61C 13/082; A61C 13/206; A61C 13/34; B29C 39/44; B29C 64/386; B33Y 50/00; B33Y 80/00; G05B 19/4099; G05B 2219/49023; G16H 50/50

See application file for complete search history.

(56) References Cited

U.S. PATENT DOCUMENTS

| | | | |
|---|---|---|---|
| 2003/0207235 A1* | 11/2003 | der Zel | B33Y 80/00 433/223 |
| 2013/0130202 A1 | 5/2013 | Vuillemot | |
| 2018/0280116 A1 | 10/2018 | Hansen et al. | |
| 2019/0231480 A1* | 8/2019 | Moore, III | B33Y 80/00 |
| 2020/0100871 A1* | 4/2020 | Wang | G01N 33/442 |
| 2021/0338390 A1* | 11/2021 | Cowburn | A61C 5/77 |

FOREIGN PATENT DOCUMENTS

WO    WO-2022253429 A1  * 12/2022

* cited by examiner

*Primary Examiner* — Chad G Erdman
(74) *Attorney, Agent, or Firm* — Perry + Currier

(57) ABSTRACT

The invention relates to a computer-implemented method for providing a set of layer-specific molding matrices for reconstructing layer-by-layer one or more teeth of a set of teeth in a patient's oral cavity. The set of layer-specific molding matrices comprises two or more layer-specific molding matrices. Each of the layer-specific molding matrices is configured for being arranged on the set of teeth and for casting a different layer of the one or more teeth to be reconstructed with a layer-specific reconstruction material inserted into the respective layer-specific molding matrix. The respective layer-specific molding matrix defines a 3D geometric form of the respective layer being casted.

31 Claims, 18 Drawing Sheets

SET OF LAYER-SPECIFIC MOLDING MATRICES

The invention relates to the field of dental technology. More particularly, the invention relates to a computer-implemented method for providing a set of layer-specific molding matrices for reconstructing layer-by-layer one or more teeth of a set of teeth in a patient's oral cavity. The invention furthermore relates to a computer device and a computer program product for providing a set of layer-specific molding matrices for reconstructing layer-by-layer one or more teeth of a set of teeth in a patient's oral cavity as well as to a manufacturing system comprising the computer device. Furthermore, the invention relates to a set of layer-specific molding matrices for reconstructing layer-by-layer one or more teeth of a set of teeth in a patient's oral cavity.

Teeth may get ground down with time. Reasons may, e.g., be bruxism or other external factors resulting in a need for a reconstruction of the teeth. Ground down teeth may, e.g., be covered using veneers, which are glued onto the respective teeth. However, such veneers may last only for a limited period of time. Therefore, there is a need for a reconstruction of the tooth in such a way that it is strong, long lasting and individually adjusted to the appearance of a patient's teeth.

It is an objective to provide for a computer-implemented method, a computer device and computer program product for providing a set of layer-specific molding matrices for reconstructing layer-by-layer one or more teeth of a set of teeth in a patient's oral cavity. Furthermore, it is an objective to provide for a manufacturing system for manufacturing a set of layer-specific molding matrices for reconstructing layer-by-layer one or more teeth of a set of teeth in a patient's oral cavity. It is a further objective to provide for a set of layer-specific molding matrices for reconstructing layer-by-layer one or more teeth of a set of teeth in a patient's oral cavity.

In one aspect, the invention relates to a computer-implemented method for providing a set of layer-specific molding matrices for reconstructing layer-by-layer one or more teeth of a set of teeth in a patient's oral cavity. The set of layer-specific molding matrices comprises two or more layer-specific molding matrices. Each of the layer-specific molding matrices is configured for being arranged on the set of teeth and for casting a different layer of the one or more teeth to be reconstructed with a layer-specific reconstruction material inserted into the respective layer-specific molding matrix. The respective layer-specific molding matrix defines a 3D geometric form of the respective layer being casted.

The method comprises providing a 3D digital teeth model of the set of teeth in the patient's oral cavity comprising the one or more teeth to be reconstructed. Using the 3D digital teeth model an ordered set of 3D digital layer-specific reconstruction models is generated. Each of the 3D digital layer-specific reconstruction models according to the order adds another one of the layers to be reconstructed to the 3D digital teeth model. Using the ordered set of 3D digital layer-specific reconstruction models an ordered set of 3D digital layer-specific molding matrices is generated. Each of the 3D digital layer-specific molding matrices is a negative of one of the 3D digital layer-specific reconstruction models. The ordered set of 3D digital layer-specific molding matrices are provided as a set of templates for manufacturing the set of layer-specific molding matrices.

Examples may have the beneficial effect, that an ordered set of 3D digital layer-specific molding matrices is provided, which defines a layer-by-layer reconstruction of teeth to be reconstructed. The ordered set of 3D digital layer-specific molding matrices may be used as a set of templates for manufacturing a set of layer-specific molding matrices, each of the layer-specific molding matrices is defined by one of the 3D digital layer-specific molding matrices and configured to add another layer to the teeth to be reconstructed. Generating the 3D digital layer-specific molding matrices using a computer device may allow to adjust 3D digital layer-specific molding matrices precisely to the individual requirements of the patient. Adjusting the layer-specific molding matrices in form 3D digital models and manufacturing the actual physical layer-specific molding matrices not before the 3D digital models suitably fit the patient's individual anatomical and/or aesthetical features, e.g., as provided by the 3D digital teeth model, may ensure that the physical layer-specific molding matrices fit the patient's individual anatomical and/or aesthetical features as well. In particular, the 3D digital layer-specific molding matrices may, e.g., be adjusted such that the resulting multilayer reconstruction corresponds in form and color, at least partially, to the teeth to be reconstructed in their original state and/or to existing neighboring teeth.

Using layer-specific molding matrices for reconstructing layer-by-layer one or more teeth of a set of teeth in a patient's oral cavity may facilitate execution of a multilayer reconstruction, since the 3D geometrical form of each of the layer-specific reconstruction steps may be defined by one of the layer-specific molding matrices. Individual layers do not have to be formed by hand, but are rather formed using the layer-specific molding matrices. This may reduce the susceptibility to errors, enable a faster application of the layer-specific reconstruction material and ensure precise achievement of a form of the layer being reconstructed as predefined by the layer-specific molding matrices used to apply the layer-specific reconstruction material.

Here, an ordered set refers to a set comprising a plurality of elements, which are each assigned to a place in an order or sequence. Thus, there is a first element according to the order, a second element according to the order, and so on. The layer-by-layer reconstruction may be defined by an ordered set of 3D digital layer-specific reconstruction models and/or by an ordered set of 3D digital layer-specific molding matrices. Each of the 3D digital layer-specific molding matrices being a negative of one of the 3D digital layer-specific reconstruction models. The ordered set of 3D digital layer-specific reconstruction models comprises a plurality of 3D digital layer-specific reconstruction models, e.g., two, three, or four models. According to the order, a first one of the 3D digital layer-specific reconstruction models adds a first layer to be reconstructed to the teeth of the 3D digital teeth model to be reconstructed. A second one of the 3D digital layer-specific reconstruction models adds a second layer to be reconstructed to the teeth of the first one of the first 3D digital layer-specific reconstruction models and so on. In case of a third or fourth 3D digital layer-specific reconstruction model, third or fourth 3D digital layer-specific reconstruction model adds a third or fourth layer to be reconstructed to the teeth of the second or third 3D digital teeth model, respectively. Thus, each of the 3D digital layer-specific reconstruction models according to the order adds another one of the layers to be reconstructed to the 3D digital teeth model. The first 3D digital layer-specific reconstruction model may correspond to the 3D digital teeth model plus one layer added, the second 3D digital layer-specific reconstruction model may correspond to the 3D digital teeth model plus two layers added, the third 3D digital layer-specific reconstruction model may correspond to the 3D digital teeth model plus three layers added and so on. In other words, the n-th 3D digital layer-specific reconstruction model according to the order of the set may correspond to the 3D digital teeth model plus n layers added with n being a natural number, i.e., a positive integer.

The 3D digital layer-specific molding matrices are assigned to the same order as the 3D digital layer-specific reconstruction models, since each of the 3D digital layer-specific molding matrices of the ordered set of 3D digital layer-specific molding matrices is assigned to one of the 3D digital layer-specific reconstruction models of the set of 3D digital layer-specific reconstruction models. Thus, each of the 3D digital layer-specific molding matrices according to the order defines a layer-specific molding matrix configured for adding another one of the layers to the teeth to be reconstructed starting with a tooth setup as defined by the 3D digital teeth model. The first 3D digital layer-specific molding matrix may define a layer-specific molding matrix for adding a first layer to the teeth as defined by 3D digital teeth model, the second 3D digital layer-specific molding matrix may define a layer-specific molding matrix for adding a second layer after the first layer has been added, the third 3D digital layer-specific molding matrix defines a layer-specific molding matrix for adding a third layer after the second layer has been added and so on. In other words, the n-th digital layer-specific molding matrix defines an n-th layer-specific molding matrix configured for adding an n-th layer to the teeth to be reconstructed according to an order the layers of the multilayer reconstruction to be implemented with n being a natural number, i.e., a positive integer.

The layer-specific molding matrices may be used to reconstruct teeth, which got ground down, e.g., by bruxism or other external factors. Using a multilayer reconstruction allow for a strong and long-lasting reconstruction. Using a 3D digital teeth model resembling a current state of one or more teeth to be reconstructed may enable an individually adjustment of the multilayer reconstruction to the appearance of a patient's teeth. The one or more teeth in their current state may, e.g., be teeth prepared for the reconstruction. In addition, scan data of the one or more teeth to be reconstructed before their preparation may be provided. The 3D digital teeth model may comprise one or more neighboring teeth of the patient not to be reconstructed. The 3D digital teeth model may, e.g., comprise a mandibular dental arch and/or a maxillary dental arch of the patient.

The 3D digital teeth model may be generated using scan data of the patient's oral cavity. For example, the patient's teeth in the oral cavity may be scanned using a scanner, e.g., an optical scanner. The achieved scan data may be used to provide the 3D digital teeth model of the scanned teeth of the oral cavity. Alternatively, an impression of the patient's teeth in the oral cavity, i.e., a negative imprint of the teeth may be taken. Either this impression may be scanned, e.g., using an optical scanner, or the negative imprint provided by the impression may be used to generate a positive reproduction of the patient's teeth, i.e., a 3D physical teeth model or cast, which is scanned, e.g., by the optical scanner to provide the scan data used to generate the 3D digital teeth model.

The 3D digital teeth model may further comprise soft tissue, like a gingiva, in addition to the hard tissue in form of the teeth, i.e., 3D digital teeth model may be provided in form of a 3D digital tissue model of at least a section of the patient's oral cavity. The 3D digital tissue model may be generated using scan data of the patient's oral cavity. For example, the patient's tissue in the oral cavity may be scanned using a scanner, e.g., an optical scanner. The achieved scan data may be used to provide the 3D digital tissue model of the scanned tissue of the oral cavity. Alternatively, an impression of the patient's tissue in the oral cavity, i.e., a negative imprint of hard and soft tissue may be taken. Either this impression may be scanned, e.g., using an optical scanner or the negative imprint provided by the impression may be used to generate a positive reproduction of the patient's tissue, i.e., a 3D physical tissue model or cast, which is scanned, e.g., by the optical scanner to provide the scan data used to generate the 3D digital tissue model.

The teeth to be reconstructed may, e.g., comprise one or more incisors. The teeth to be reconstructed may, e.g., comprise one or more canines. The teeth to be reconstructed may, e.g., comprise one or more mandibular teeth. The teeth to be reconstructed may, e.g., comprise one or more maxillary teeth.

The 3D digital layer-specific molding matrices may each comprises one or more recesses configured to receive the one or more teeth of the patient's oral cavity on which the layers are to be reconstructed. Each of these recesses may have a 3D geometric form, which is a negative of the tooth of the patient's oral cavity to be received by the respective recess in combination with the layer to be reconstructed by the respective layer-specific molding matrix. The teeth of the patient's oral cavity to be received in the recesses may be the initial teeth in case of a first 3D digital layer-specific molding matrix configured to reconstruct the first layer on the respective teeth. The teeth of the patient's oral cavity to be received in the recesses may be at least partially reconstructed teeth with one or more of the reconstructed layers. In case of a second 3D digital layer-specific molding matrix, the partially reconstructed teeth may be the initial teeth in combination with a first reconstructed layer. In case of a third 3D digital layer-specific molding matrix, the partially reconstructed teeth may be the initial teeth in combination with a first and second reconstructed layer and so on. Each of the recesses of the 3D digital layer-specific molding matrices may be configured such that with the tooth of the patient's oral cavity, initial tooth or partially reconstructed tooth, arranged within the respective recess hollow section remains within this recess defining a 3D geometric form of the additional layer to be reconstructed.

Furthermore, the 3D digital layer-specific molding matrices may comprise further fixating recesses for fixating the layer-specific molding matrices defined by the 3D digital layer-specific molding matrices on one or more teeth in the patient's oral cavity, which are not to be reconstructed. These teeth not to be reconstructed may, e.g., comprise one or more premolars. The teeth not to be reconstructed may, e.g., comprise one or more molars. The teeth not to be reconstructed may, e.g., comprise one or more mandibular teeth. The teeth not to be reconstructed may, e.g., comprise one or more maxillary teeth. These fixating recesses may have 3D geometric forms, which are negatives of 3D geometric forms of the teeth to be received by the respective fixating recesses. Each of the 3D digital layer-specific molding matrices may comprise identical fixating recesses ensuring a fixating of the layer-specific molding matrices defined by the 3D digital layer-specific molding matrices at identical positions within the oral cavity of the patient. Thus, during the repeated process of reconstructing layers using the different layer-specific molding matrices, for each layer being reconstructed the possibility for error in the re-positioning of the respective layer-specific molding matrix may be minimized or even excluded.

For example, the method further comprises generating using the 3D digital teeth model the ordered set of 3D digital layer-specific reconstruction models. The ordered set of 3D digital layer-specific reconstruction models is used for generating the ordered set of 3D digital layer-specific molding matrices.

For example, the 3D digital layer-specific reconstruction models may be generated one after another by adding one layer after another to the teeth to be reconstructed as defined by the 3D digital teeth model. The 3D digital teeth model in combination with a first one of the layers to be reconstructed may form a first 3D digital layer-specific reconstruction model. The 3D digital teeth model in combination with a first and a second one of the layers to be reconstructed may form a second 3D digital layer-specific reconstruction model. The 3D digital teeth model in combination with a first, as second, and a third one of the layers to be reconstructed may form a third 3D digital layer-specific reconstruction model and so on.

The layers being reconstructed, i.e., added to the teeth to be reconstructed as defined by the 3D digital teeth model, may, e.g., be generated from scratch individually adjusted to 3D geometric forms defined by the teeth to be reconstructed and/or adjusted to 3D geometric forms defined by one or more neighboring teeth. For example, pre-defined elements may be used to define the respective layers. For example, one of more artificial teeth or teeth elements may be selected from a tooth library. For example, the tooth library may define teeth elements in form of individual layers or layer sections. These teeth elements may be selected and used to generate the 3D digital layer-specific reconstruction models. For example, the teeth elements selected from the tooth library may be adjusted to the individual 3D geometric forms as defined for the teeth to be reconstructed by the 3D digital teeth model. For example, the teeth elements selected from the tooth library may be used as generic elements, which are arranged on the teeth to be reconstructed as defined by the 3D digital teeth model.

The selected teeth from the tooth library may, e.g., be defined as multilayer structures. The different layers of the multilayer structures may be used to define the 3D digital teeth models of the ordered set of 3D digital teeth models. For example, the teeth elements selected from the tooth library may be used to replace the teeth of the 3D digital teeth model, which are to be reconstructed. For example, the 3D geometric forms of the multilayer structures as defined by the selected teeth form the tooth library may be adjusted to the patient-individual anatomical structures defined by the 3D digital teeth model, e.g., the available space between neighboring teeth, within which the teeth to be reconstructed are arranged. For example, the patient-individual anatomical structures may comprise the 3D geometric forms of the teeth to be reconstructed and/or the 3D geometric forms of neighboring teeth. For example, the multilayer structure defined by the teeth selected from the tooth library may be used as generic multilayer structures, which are used to replace the teeth to be reconstructed as defined by the 3D digital teeth model.

For example, the 3D digital layer-specific reconstruction models may each correspond to the 3D digital teeth model with the teeth to be reconstructed replaced by layer-specific multilayer structures selected from the tooth library. The layer-specific multilayer structures may comprise for each of the 3D digital layer-specific reconstruction models a different number of layers. The number of layers may depend on the position of the respective 3D digital layer-specific reconstruction models within the order as defined by the ordered set of 3D digital layer-specific reconstruction models. For example, a last 3D digital layer-specific reconstruction model according to the order as defined by the ordered set of 3D digital layer-specific reconstruction models may comprise all the layers of the multilayer structures. Each preceding 3D digital layer-specific reconstruction model according to the order as defined by the ordered set of 3D digital layer-specific reconstruction models may comprise one layer less, starting with an outermost layer of each of the multilayer structures.

For example, a final reconstruction form may be defined for each of the teeth to be reconstructed as provided by the 3D digital teeth model. The final reconstruction forms may, e.g., be defined for each of the respective teeth from scratch. The final reconstruction forms may, e.g., be defined for each of the respective teeth by an artificial tooth selected from a tooth library. For example, the teeth to be reconstructed within the 3D digital teeth model may be selected using a segmentation algorithm and replaced by the artificial teeth selected from the tooth library.

The artificial teeth selected from the tooth library may be used as generic teeth to replace the teeth to be reconstructed as defined by the 3D digital teeth model or the teeth selected from the tooth library may be adjusted to the patient-individual anatomical structures as defined by the 3D digital teeth model. The 3D digital teeth model with the final reconstruction forms for the teeth to be reconstructed added may define a last 3D digital layer-specific reconstruction model according to the order as defined by the ordered set of 3D digital layer-specific reconstruction models. Starting with the final reconstruction the forms of the layers of the teeth to be reconstructed may be defined. Thus, starting with an outermost layer, the inner layers of the multilayer reconstruction may be defined. Each preceding 3D digital layer-specific reconstruction model according to the order as defined by the ordered set of 3D digital layer-specific reconstruction models may comprise one of the defined layers less, starting with an outermost layer.

As template for colors and/or degrees of transparency of the layers to be reconstructed, e.g., measurements of the teeth to be reconstructed may be used. The teeth to be reconstructed as defined by the 3D digital teeth model may, e.g., be teeth prepared for the layer-by-layer reconstruction. In order to prepare a tooth to be reconstructed layer-by-layer, one or more parts, e.g., layer sections, of the tooth may be removed. A tooth, which got ground down, may comprise an irregular structure. For example, the tooth may comprise different irregular remainders of different layers. In order to be able, to reconstruct layers with a regular continuous structure, parts, e.g., layer sections, of the tooth may have to be removed. Thus, it may be enabled reconstruct larger, more regular parts of the reconstruction layers. In case the teeth to be reconstructed are prepared, scan data of the respective teeth before the preparation may, e.g., be used to define colors and/or degrees of transparency of the layers to be reconstructed. As template for colors and/or degrees of transparency of the layers to be reconstructed, e.g., measurements of neighboring teeth may be used.

As templates for the layers to be reconstructed, e.g., for the thicknesses of the layers and/or for parts of the 3D geometric forms of the layers to be reconstructed, measurements of the teeth to be reconstructed may be used. In case the teeth to be reconstructed are prepared, scan data of the respective teeth before the preparation may, e.g., be used to determine the geometric form and/or the thicknesses of the layers of the teeth before the preparation. For determining the geometric form and/or the thicknesses of the layers, e.g., scan data of a scan of inner structures of the respective teeth may be used. For acquiring scan data of the inner structures of the respective teeth, e.g., a scan using radiation in the infrared frequency spectrum, like near-infrared radiation, e.g., with a wavelength in the range from 0.75 to 1.4 μm, or X-rays may be used. As templates for the layers to be reconstructed, e.g., for the thicknesses of the layers and/or for parts of the 3D geometric forms of the layers to be reconstructed, measurements of neighboring teeth may, e.g., be used. For determining the geometric form and/or the thicknesses of the layers, e.g., scan data of a scan of inner structures of the respective neighboring teeth may be used. For acquiring scan data of the inner structures of the respective neighboring teeth, e.g., a scan using radiation in the infrared frequency spectrum, like near-infrared radiation, e.g., with a wavelength in the range from 0.75 to 1.4 μm, or X-rays may be used.

For example, the method further comprises manufacturing the set of layer-specific molding matrices using the ordered set of 3D digital layer-specific molding matrices as templates. Each of the manufactured layer-specific molding matrices of the set of layer-specific molding matrices is a physical copy of one of the templates.

Examples may have the beneficial effect, that the set of layer-specific molding matrices may be provided for reconstructing layer-by-layer the one or more teeth of the set of teeth in the patient's oral cavity.

For example, the set of layer-specific molding matrices is manufactured using at least one of the following: machining, 3D printing, casting.

For example, the layer-specific molding matrices of the set of layer-specific molding matrices may be manufactured using one or more machining devices configured to manufacture molding matrices by processing blanks. Multiple layer-specific molding matrices may, e.g., be manufactured successively using the same machining device or in parallel using one or more machining devices. For example, the layer-specific molding matrices of the set of layer-specific molding matrices may be manufactured using one or more 3D printing devices, i.e., printers, configured to print molding matrices. Multiple layer-specific molding matrices may, e.g., be manufactured successively using the same 3D printing device or in parallel using one or more 3D printing devices.

For example, the set of 3D digital layer-specific molding matrices may be used as a set of positives to define a set of negatives of the layer-specific molding matrices in form of negative 3D digital layer-specific molding matrices. The set of negative 3D digital layer-specific molding matrices may be used to manufacture, e.g., using machining or 3D printing, a set of matrices. Each of the manufactured matrices may be configured to cast one of the layer-specific molding matrices of the set of layer-specific molding matrices. The resulting layer-specific molding matrices may then be usable for reconstructing layer-by-layer the one or more teeth of the set of teeth in the patient's oral cavity.

For example, the set of layer-specific molding matrices comprises two layer-specific molding matrices. The two layer-specific molding matrices may, e.g., be configured for reconstructing a vestibular enamel layer and an oral enamel layer. The two layer-specific molding matrices may, e.g., be configured for reconstructing a vestibular dentin layer and an oral enamel layer.

For example, the set of layer-specific molding matrices comprises three layer-specific molding matrices. The three layer-specific molding matrices may, e.g., be configured for reconstructing a vestibular enamel layer, a vestibular dentin layer and an oral enamel layer.

For example, the set of layer-specific molding matrices comprises layer-specific molding matrices configured for casting one or more of the following types of layers: an oral enamel layer, a vestibular enamel layer, an oral dentin layer, a vestibular dentin layer. The oral enamel layer may, e.g., be a lingual or palatal enamel layer. The vestibular enamel layer may, e.g., be a labial or buccal enamel layer. The oral dentin layer may, e.g., be a lingual or palatal dentin layer. The vestibular dentin layer may, e.g., be a labial or buccal dentin layer.

For example, thicknesses of the layers added by the 3D digital layer-specific reconstruction models depend on at least one of the following: a target color of the one or more teeth to be reconstructed, target degrees of transparency of the reconstructed layers of the one or more teeth to be reconstructed, a target form of the one or more teeth to be reconstructed, minimum thickness required by the layer-specific reconstruction material intended to be used for casting the respective layer.

Examples may have the beneficial effect, that the thicknesses of the layers of the multilayer reconstruction of a tooth may be adjusted such that a resulting color matches a target color of the tooth to be reconstructed. Thus, a natural aesthetical appearance of the reconstructed tooth may be achieved. The thicknesses of the layers of the multilayer reconstruction of a tooth may be adjusted such that the resulting degrees of transparency of the reconstructed layers match target degrees of transparency of the layers of the tooth to reconstructed. Thus, a natural aesthetical appearance of the reconstructed tooth may be achieved. The thicknesses of the layers of the multilayer reconstruction of a tooth may be adjusted such that a resulting form of the reconstructed tooth matches a target form for the tooth. Thus, a natural aesthetical appearance of the reconstructed tooth may be achieved. The thicknesses of the layers of the multilayer reconstruction of a tooth may be adjusted such that the resulting thicknesses are each equal to or larger than minimum thickness required by the layer-specific reconstruction material intended to be used for reconstructing the respective layer.

For example, a database may be provided comprising data for a plurality of layer-specific reconstruction materials. For each type of layer of a plurality of different types of layers, one or more reconstruction materials may be identified as layer-specific reconstruction materials. For each of the layer-specific reconstruction material a minimum thickness required by the layer-specific reconstruction material in order to ensure a sufficient structural strength may be defined.

The database may be used to provide for the set of the 3D digital layer-specific reconstruction models a suggestion of a layer-specific reconstruction material for each of the reconstruction layers defined by 3D digital layer-specific reconstruction models. Each of the 3D digital layer-specific reconstruction models may define a 3D geometric form of a layer to be reconstructed. The 3D geometric form may have a minimum thickness. The minimum thickness may be a smallest thickness of the layer as defined by the 3D geometric form. The suggestion of layer-specific reconstruction materials may suggest layer-specific reconstruction materials assigned with a minimum thickness equal to or smaller than the minimum thickness defined by the 3D geometric form of the layer for which the respective layer-specific reconstruction material is suggested. Thus, it may be ensured that a layer formed with the suggested layer-specific reconstruction material as defined by the 3D geometric form of the respective layer has an actual minimum thickness which is equal to or larger than a minimum thickness required by the layer-specific reconstruction material in order to ensure a sufficient structural strength.

For example, the layer-specific reconstruction material defined in the database for a specific type of layer may be ordered according to an order indicating an order of preference regarding the usage of the respective layer-specific reconstruction material for the respective type of layer. For example, for each of the layers to be reconstructed, the first layer-specific reconstruction material according to the order with an assigned minimum thickness equal to or smaller than the minimum thickness defined by the 3D geometric form of the respective layer to be reconstructed may be provided as a suggestion.

The order of preference may be a pre-defined order of preference to which all the layer-specific reconstruction material stored in the database are assigned. The order of preference may be received as input as an individual order of preference defined for an individual patient. The order of preference may be received as input for all the layer-specific reconstruction materials stored in the database or for a selection of layer-specific reconstruction materials to be taken into account for an individual patient. The selection of layer-specific reconstruction materials may comprise layer-specific reconstruction materials selected from the layer-specific reconstruction materials stored in the database.

For example, all the layer-specific reconstruction materials stored in the database may be taken into account for providing a suggestion of layer-specific reconstruction materials. For example, only a selection of layer-specific reconstruction materials selected from the layer-specific reconstruction materials stored in the database may be taken into account for the analysis of potential layer-specific reconstruction materials.

Furthermore, different color and/or degrees of transparency may be defined in the database and assigned to each of the layer-specific reconstruction materials. For each of the colors and/or degrees of transparency a thickness of the respective reconstruction material or a range of thickness of the respective reconstruction material may be defined, with which the respective color and/or degree of transparency may be achieved.

For example, the set of the 3D digital layer-specific reconstruction models may further define for each of the 3D digital layer-specific reconstruction models of the set of the 3D digital layer-specific reconstruction models a color and/or degree of transparency of the layer defined by the respective 3D digital layer-specific reconstruction model. The suggestion of layer-specific reconstruction materials may suggest layer-specific reconstruction materials assigned not only with a sufficient minimum thickness, but which are also configured to provide the desired color and/or degree of transparency for a thickness or range of thicknesses comprised by the 3D geometric form of the layer to be reconstructed as defined by the respective 3D digital layer-specific reconstruction model. Thus, it may be ensured that a layer formed with the suggested layer-specific reconstruction material as defined by the 3D geometric form of the respective layer not only has a sufficient thickness, but also has a thickness, which allows the layer being reconstructed to have a desired color and/or degree of transparency.

For the suggestions, as described above, also an order of preferences may be taken into account and for each layer. For example, the layer-specific reconstruction material may be suggested, which according to the order is the first of the layer-specific reconstruction material satisfying all the requirement regarding the thickness of the layer.

For example, the database may be used to determine the 3D digital layer-specific reconstruction models of the set of 3D digital layer-specific reconstruction models. For example, the database may be used to provide a suggestion for the thicknesses of the reconstruction layers defined by the 3D digital layer-specific reconstruction models. For example, definitions of the colors and/or degrees of transparency for the layers defined by the 3D digital layer-specific reconstruction models may be provided. In addition, e.g., a selection of the layer-specific reconstruction materials and/or an order of preference of the layer-specific reconstruction materials may be provided. Using these definitions and, e.g., the selection and/or order of preference, for each of the layers defined by the 3D digital layer-specific reconstruction models a thickness and a layer-specific reconstruction material to be used may be suggested such that using the suggested layer-specific reconstruction materials with the suggested thickness for the respective layers, the colors and/or degrees of transparency as defined may be implemented. The thicknesses may be selected such that the thicknesses of the layers reconstructed add up resulting in one or more reconstructed teeth, each tooth with a size and geometrical shape as defined by the last 3D digital layer-specific reconstruction model of the ordered set of 3D digital layer-specific reconstruction models according to the order assigned to the ordered set.

For example, a machine learning module may be provided, which is trained to provide an ordered set of 3D digital layer-specific reconstruction models or an ordered set of 3D digital layer-specific molding matrices defining layers with thicknesses that satisfy a minimum criterion for particular layer-specific reconstruction materials as described above and/or with thicknesses ensuring desired colors and/or degrees of thickness for the layers being reconstructed. The minimum thicknesses and/or the colors and/or the degrees of thickness may be provided in addition to the 3D digital teeth model to the machine learning module, in order to receive the ordered set of 3D digital layer-specific reconstruction models or an ordered set of 3D digital layer-specific molding matrices as output in response. For example, the colors and/or the degrees of thickness may be provided as part of the 3D digital teeth model. For example, the 3D digital teeth model may provide measured colors and/or degrees of thickness of the one or more teeth to be reconstructed and/or measured colors and/or degrees of thickness of one or more neighboring teeth.

For example, the layer-specific molding matrices comprises one or more injection channels configured for inserting the layer-specific reconstruction material by injecting the layer-specific reconstruction material into the layer-specific molding matrices.

Examples may have the beneficial effect, that the injection channels may facilitate injecting the layer-specific reconstruction material into the respective layer-specific molding matrix of the set of layer-specific molding matrices. For injecting the layer-specific reconstruction material, an injection device may be used, e.g., a reciprocating pump, like a syringe. The injection channels may each, e.g., comprise a mouth. The mouths of the injection channels may, e.g., be arranged on occlusal sides of the layer-specific molding matrices.

The resulting layer-specific molding matrices manufactured using the 3D digital layer-specific molding matrices as templates, may thus each comprise one or more injection channels configured for inserting the layer-specific reconstruction material by injecting the layer-specific reconstruction material into the layer-specific molding matrices.

For example, the layer-specific molding matrices comprises one or more venting channels configured for letting out air, when the layer-specific reconstruction material is inserted by injecting the layer-specific reconstruction material into the layer-specific molding matrices.

Examples may have the beneficial effect, that the venting channels may ensure an effective venting of the respective layer-specific molding matrices of the set of layer-specific molding matrices, when the layer-specific reconstruction material is inserted by injecting the layer-specific reconstruction material into the layer-specific molding matrices. Thus, air bubbles and any other irregularities within the injected layer-specific reconstruction material may be avoided.

The resulting layer-specific molding matrices manufactured using the 3D digital layer-specific molding matrices as templates, may thus each comprise one or more venting channels configured for letting out air, when the layer-specific reconstruction material is inserted by injecting the layer-specific reconstruction material into the layer-specific molding matrices.

For example, the method further comprises generating at least one 3D digital model of a mantle shell for at least one of the 3D digital layer-specific molding matrices. The 3D digital model of the mantle shell comprises a reception. The reception is a negative of an outer 3D geometrical form of the respective 3D digital layer-specific molding matrix. The reception is, e.g., configured for receiving the respective 3D digital layer-specific molding matrix. The 3D digital model of the mantle shell is configured to be slipped over the respective 3D digital layer-specific molding matrix arranged on one of the 3D digital layer-specific reconstruction models and providing structural support to the respective 3D digital layer-specific molding matrix. The at least one 3D digital model of the mantle shell is provided as a template for manufacturing a physical copy of the 3D digital model of the mantle shell using the 3D digital model of the mantle shell as a template.

Examples may have the beneficial effect, that the mantle shell may be used to provide stability to one or more of the layer-specific molding matrices of the set of layer-specific molding matrices. For example, a mantle shell may be provided for the set of layer-specific molding matrices. The single mantle shell may be configured to be slipped over each of the layer-specific molding matrices of the set of layer-specific molding matrices in order to provide structural support to the respective 3D digital layer-specific molding matrix, over which it is slipped. For example, the mantle shell may be a generic mantle shell configured to be slipped over layer-specific molding matrices of different sets of layer-specific molding matrices. For example, the mantle shell may be a may be a set-specific mantle shell, configured to be slipped over the layer-specific molding matrices of a specific set of layer-specific molding matrices.

For example, a plurality of matrix-specific mantle shells may be provided. For example, a matrix-specific mantle shell may be provided for each of the layer-specific molding matrices of the set of layer-specific molding matrices.

The one or more mantle shell may, e.g., be manufactured from a material more rigid than a material, from which the layer-specific molding matrices of the set of layer-specific molding matrices are manufactured. The inner surfaces of the mantle shell in contact with the outer surfaces of one of the layer-specific molding matrices of the set of layer-specific molding matrices may have a simpler 3D geometry than the inner surfaces of the respective layer-specific molding matrix in contact with surfaces of the natural tissue in the patient's oral cavity. The simpler 3D geometry, e.g., with straight faces, may facilitate a removal of the mantle shell from the layer-specific molding matrix, despite of its more rigid material. The more flexible material of the layer-specific molding matrix may facilitate a removal of the layer-specific molding matrix from the natural tissue teeth in the patient's oral cavity, in particular the teeth, despite of its more complex geometry.

For example, the reception comprises straight internal side-faces. The respective 3D digital layer-specific molding matrix comprises straight external side-faces in contact with the straight internal side-faces of the mantle shell, when the mantle shell is slipped over the respective layer-specific molding matrix.

Examples may have the beneficial effect, that the straight internal side-faces of the mantle shell may facilitate a removal from the layer-specific molding matrix with the straight external side-faces.

For example, the reception of the at least one 3D digital model of the mantle shell comprises a U-shaped cross section. The outer 3D geometrical form of the respective 3D digital layer-specific molding matrix comprises a U-shaped cross section in contact with the straight internal side-faces of the mantle shell, when the mantle shell is slipped over the respective layer-specific molding matrix.

For example, the method further comprises manufacturing the physical copy of the at least one 3D digital model of the mantle shell using the at least one 3D digital model of the mantle shell as a template.

Examples may have the beneficial effect, that the mantle shell is provided. The mantle shell may be configured to be slipped over one of the layer-specific molding matrices of the set of layer-specific molding matrices arranged on the one or more teeth of the set of teeth in the patient's oral cavity. The mantle shell may be configured to provide structural support to the respective 3D digital layer-specific molding matrix, over which it is slipped.

For example, the physical copy of the at least one 3D digital model of the mantle shell is manufactured using at least one of the following: machining, 3D printing, casting.

For example, the mantle shell may be manufactured using a machining device configured to manufacture the mantle shell by processing a blank. For example, the mantle shell may be manufactured using a 3D printing device, i.e., printer, configured to print the mantle shell. For example, the 3D digital model of the mantle shell may be used as a positive to define a negative of the mantle shell in form of negative 3D digital model of the mantle shell. The negative 3D digital model of the mantle shell may be used to manufacture, e.g., using machining or 3D printing, a matrix for casting the mantle shell. The resulting mantle shell may be configured to be slipped over one of the layer-specific molding matrices of the set of layer-specific molding matrices arranged on the one or more teeth of the set of teeth in the patient's oral cavity. The mantle shell may be configured to provide structural support to the respective 3D digital layer-specific molding matrix, over which it is slipped.

For example, the physical copy of the at least one 3D digital model of the mantle shell is manufactured using a material which is more rigid than a material used for manufacturing the layer-specific molding matrices.

Examples may have the beneficial effect, that the mantle shell may provide stability to the layer-specific molding matrices, while the layer-specific molding matrices of the set of layer-specific molding matrices due to their higher flexibility are easier removable from the one or more teeth in the patient's oral cavity.

For example, the 3D digital model of the mantle shell comprises one or more injection channels configured for inserting the layer-specific reconstruction material by injecting the layer-specific reconstruction material into the layer-specific molding matrix, over which the 3D digital model of the mantle shell is slipped.

The injection channels of the 3D digital model of the mantle shell may be aligned with the injection channels of the 3D digital layer-specific molding matrix. Examples may have the beneficial effect, that the injection channels of the 3D digital model of the mantle shell may facilitate injecting of the layer-specific reconstruction material into the layer-specific molding matrix, over which the mantle shell is slipped.

The resulting mantle shell may thus comprise one or more injection channels configured for inserting the layer-specific reconstruction material by injecting the layer-specific reconstruction material into the layer-specific molding matrix, over which the model of the mantle shell is slipped. The injection channels of the mantle shell may be aligned with the injection channels of the layer-specific molding matrix. For injecting the layer-specific reconstruction material, an injection device may be used, e.g., a reciprocating pump, like a syringe. The injection channels may each, e.g., comprise a mouth. The mouths of the injection channels may, e.g., be arranged on an occlusal side of the mantle shell.

For example, the 3D digital model of the mantle shell comprises one or more venting channels configured for letting out air, when the layer-specific reconstruction material is inserted by injecting the layer-specific reconstruction material into the layer-specific molding matrix, over which the 3D digital model of the mantle shell is slipped.

Examples may have the beneficial effect, that the venting channels may ensure an effective venting of the respective layer-specific molding matrices of the set of layer-specific molding matrices, when the layer-specific reconstruction material is inserted by injecting the layer-specific reconstruction material into the layer-specific molding matrices. Thus, air bubbles and any other irregularities within the injected layer-specific reconstruction material may be avoided.

The venting channels of the 3D digital shell model may be aligned with the venting channels of the 3D digital layer-specific molding matrix. Examples may have the beneficial effect, that the venting channels may ensure an effective venting of the layer-specific molding matrices manufactured using the 3D digital layer-specific molding matrices of the set of 3D digital layer-specific molding matrices as templates, when the layer-specific reconstruction material being injected into the layer-specific molding matrices generates an overpressure within the layer-specific molding matrices relative to the environment of the layer-specific molding matrices.

The resulting mantle shell may thus comprise one or more venting channels configured for letting out air, when the layer-specific reconstruction material is inserted by injecting the layer-specific reconstruction material into the layer-specific molding matrix, over which the mantle shell is slipped. The venting channels of the mantle shell may be aligned with the venting channels of the layer-specific molding matrix. The mouths of the injection channels may, e.g., be arranged on an occlusal side of the mantle shell.

For example, an individual 3D digital model of the mantle shell is generated and provided for each of the 3D digital layer-specific molding matrices of the ordered set of 3D digital layer-specific molding matrices.

Examples may have the beneficial effect of providing an individual 3D digital model of the mantle shell for each of the 3D digital layer-specific molding matrices of the set of 3D digital layer-specific molding matrices. Furthermore, the individual 3D digital models of the mantle shells may be used as templates for manufacturing individual mantle shells. Thus, individual mantle shell may be provided for each of layer-specific molding matrices of the set of layer-specific molding matrices.

For example, a single common 3D digital model of the mantle shell is generated and provided for all the 3D digital layer-specific molding matrices of the ordered set of 3D digital layer-specific molding matrices.

Examples may have the beneficial effect of providing a single common 3D digital model of the mantle shell for all the 3D digital layer-specific molding matrices of the set of 3D digital layer-specific molding matrices. Furthermore, the single common 3D digital model of the mantle shell may be used as a template for manufacturing a single common mantle shell for all the layer-specific molding matrices of the set of layer-specific molding matrices. Thus, a single common mantle shell may be provided for all the layer-specific molding matrices of the set of layer-specific molding matrices.

For example, a first trained machine learning module is used for generating the 3D digital layer-specific molding matrices of the ordered set of 3D digital layer-specific molding matrices. The first trained machine learning module is configured to provide the 3D digital layer-specific molding matrices as output in response to receiving the 3D digital teeth model as input.

Examples may have the beneficial effect, that the trained machine learning module may be used for generating the set of 3D digital layer-specific molding matrices base on the 3D digital teeth model.

Each of the 3D digital layer-specific molding matrices may be configured to add another layer to the teeth being reconstructed. The thicknesses of the layers being reconstructed by the layer-specific molding matrices defined by the of 3D digital layer-specific molding matrices, which are provided by the trained machine learning module, may be configured to achieve at least one of the following: a target color of the one or more teeth to be reconstructed, target degrees of transparency of the reconstructed layers of the one or more teeth to be reconstructed, a target form of the one or more teeth to be reconstructed, a minimum thickness required by the layer-specific reconstruction material intended to be used for reconstructing the respective layer. In other word, the trained machine learning module may be trained accordingly.

In addition, further data may be provided as input to the trained machine learning module. For example, the input provided to the machine learning module may further comprise one or more of the following: a target color of the one or more teeth to be reconstructed, e.g., defined by the color of a neighboring tooth or by a selected color from set of predefined colors, target degrees of transparency of the reconstructed layers of the one or more teeth to be reconstructed, e.g., defined by the degree of transparency of layers of a neighboring tooth, a target form of the one or more teeth to be reconstructed, one or more minimum thicknesses required by the layer-specific reconstruction materials intended to be used for casting one or more respective layers, a number of layers to be reconstructed, definition of types of layers to be reconstructed.

For example, the method further comprises providing the first trained machine learning module. The providing of the first trained machine learning module comprises providing a first machine learning module to be trained. A set of first training datasets for training the first machine learning module to be trained is provided. Each first training dataset comprises a first 3D digital training teeth model and an ordered set of 3D digital layer-specific training molding matrices. The first machine learning module to be trained is trained to provide the 3D digital layer-specific training molding matrices of the ordered set of 3D digital layer-specific training molding matrices of the first training datasets as output in response to receiving the first 3D digital training teeth models of the respective first training datasets as input.

The first machine learning module to be trained may, e.g., be an untrained machine learning module, a pre-trained machine learning module or a partially trained machine learning module. The machine learning module being trained may be an untrained machine learning module, which is trained from scratch. Alternatively, the machine learning module being trained may be a pre-trained or partially trained machine learning module. In general, it may not be necessary to start with an untrained machine learning module, e.g., in deep learning. For example, one may start with a pre-trained or partially trained machine learning module. The pre-trained or partially trained machine learning module may have been pre-trained or partially trained for the same or a similar task. Using a pre-trained or partially trained machine learning may, e.g., enable a faster training of the trained machine learning module to be trained, i.e., the training may converge faster. For example, transfer learning may be used for training a pre-trained or partially trained machine learning module. Transfer learning refers to a machine learning process, which rather than starting the learning process from scratch starts from patterns that have been previously learned, when solving a different problem. This way previous learnings may, e.g., be leveraged, avoiding to start from scratch. A pre-trained machine learning module is a machine learning module that was trained previously, e.g., on a large benchmark dataset to solve a problem similar to the one to be solved by the additional learning. In case of a pre-trained machine learning module a previous learning process has been completed successfully. A partially trained machine learning module is a machine learning module, which has been partially trained, i.e., the training process may not have been completed yet. A pre-trained or partially machine learning module may, e.g., be import and trained to be used for the purposes disclosed herein.

Examples may have the beneficial effect, that by training the machine learning module to be trained, the machine learning module may be configured to provide the 3D digital layer-specific molding matrices as output in response to receiving the 3D digital teeth model as input. In order to achieve this goal, a set, i.e., a plurality, of suitable training datasets is provided. Each of the training datasets may comprise a 3D digital training teeth model defining the input and an ordered set of 3D digital layer-specific training molding matrices defining the output to be provided by the machine learning module. In addition, further data may be provided as input. For example, the training input data provided by the training datasets may further comprise one or more of the following: a target color of the one or more teeth to be reconstructed, e.g., defined by the color of a neighboring tooth or by a selected color from set of predefined colors, target degrees of transparency of the reconstructed layers of the one or more teeth to be reconstructed, e.g., defined by the degree of transparency of layers of a neighboring tooth, a target form of the one or more teeth to be reconstructed, one or more minimum thicknesses required by the layer-specific reconstruction materials intended to be used for casting one or more respective layers, a number of layers to be reconstructed, definition of types of layers to be reconstructed.

For example, a second trained machine learning module is used for generating the 3D digital layer-specific reconstruction models of the ordered set of 3D digital layer-specific reconstruction models. The second trained machine learning module is configured to provide the 3D digital layer-specific reconstruction models as output in response to receiving the 3D digital teeth model as input.

Examples may have the beneficial effect, that the trained machine learning module may be used for providing the 3D digital layer-specific reconstruction models, which are used for generating the set of 3D digital layer-specific molding matrices. Each of the 3D digital layer-specific molding matrices is a negative of one of the 3D digital layer-specific reconstruction models.

The 3D digital layer-specific reconstruction models may define thicknesses of layers being added by the 3D digital layer-specific reconstruction models, i.e., thicknesses of layers being reconstructed by the layer-specific molding matrices of the set of layer-specific molding matrices. The thicknesses of the layers defined by the 3D digital layer-specific reconstruction models provided by the trained machine learning module may be configured to achieve at least one of the following: a target color of the one or more teeth to be reconstructed, target degrees of transparency of the reconstructed layers of the one or more teeth to be reconstructed, a target form of the one or more teeth to be reconstructed, minimum thickness required by the layer-specific reconstruction material intended to be used for reconstructing the respective layer. In other word, the trained machine learning module may be trained accordingly.

In addition, further data may be provided as input to the trained machine learning module. For example, the input provided to the machine learning module may further comprise one or more of the following: a target color of the one or more teeth to be reconstructed, e.g., defined by the color of a neighboring tooth or by a selected color from set of predefined colors, target degrees of transparency of the reconstructed layers of the one or more teeth to be reconstructed, e.g., defined by the degree of transparency of layers of a neighboring tooth, a target form of the one or more teeth to be reconstructed, one or more minimum thicknesses required by the layer-specific reconstruction materials intended to be used for casting one or more respective layers, a number of layers to be reconstructed, definition of types of layers to be reconstructed.

For example, the method further comprises providing the second trained machine learning module. The providing of the second trained machine learning module comprises providing a second machine learning module to be trained. A set of second training datasets for training the untrained second machine learning module is provided. Each second training dataset comprises a second 3D digital training teeth model and an ordered set of 3D digital layer-specific training reconstruction models. The second machine learning module to be trained is trained to provide the 3D digital layer-specific training reconstruction models of the ordered set of 3D digital layer-specific training reconstruction models of the second training datasets as output in response to receiving the second 3D digital training teeth models of the second respective training datasets as input.

The second machine learning module to be trained may, e.g., be an untrained machine learning module, a pre-trained machine learning module or a partially trained machine learning module.

Examples may have the beneficial effect, that by training the machine learning module to be trained, the machine learning module may be configured to provide the 3D digital layer-specific training reconstruction models as output in response to receiving the 3D digital teeth model as input. The 3D digital layer-specific training reconstruction models may be used to generate the 3D digital layer-specific molding matrices. In order to achieve this goal, a set, i.e., a plurality, of suitable training datasets is provided. Each of the training datasets may comprise a 3D digital training teeth model defining the input and an ordered set of 3D digital layer-specific training reconstruction models defining the output to be provided by the machine learning module. In addition, further data may be provided as input. For example, the training input data provided by the training datasets may further comprise one or more of the following: a target color of the one or more teeth to be reconstructed, e.g., defined by the color of a neighboring tooth or by a selected color from set of predefined colors, target degrees of transparency of the reconstructed layers of the one or more teeth to be reconstructed, e.g., defined by the degree of transparency of layers of a neighboring tooth, a target form of the one or more teeth to be reconstructed, one or more minimum thicknesses required by the layer-specific reconstruction materials intended to be used for casting one or more respective layers, a number of layers to be reconstructed, definition of types of layers to be reconstructed.

The term "machine learning" (ML) refers to a computer algorithm used to extract useful information from training data sets by building probabilistic models, which are referred to as machine learning modules or models, in an automated way. A machine learning module may also be referred to as a predictive model. Machine learning algorithms build a mathematical model based on sample data, known as "training data", in order to make predictions or decisions without being explicitly programmed to perform the task. The machine learning may be performed using a learning algorithm such as supervised or unsupervised learning. The machine learning may be based on various techniques such as clustering, classification, linear regression, reinforcement, self-learning, support vector machines, neural networks, etc. A machine learning module may, e.g., be a data structure or program such as a neural network, in particular a convolutional neural network, a support vector machine, a decision tree, a Bayesian network etc. The machine learning module may be adapted to predict an unmeasured value, e.g., a thickness of a layer being added by a 3D digital layer-specific reconstruction model provided as output by the trained machine learning module from other, known values, e.g., a 3D digital teeth model of the set of teeth in the patient's oral cavity comprising the one or more teeth to be reconstructed. According to an example, the machine learning module comprises a deep learning model.

For example, the set of teeth comprises teeth of at least one of the following: a mandibular dental arch, a maxillary dental arch. Examples may have the beneficial effect, that the layer-specific molding matrices of the set of layer-specific molding matrices may be configured for casting layers of teeth of the mandibular dental arch and/or the maxillary dental arch.

For example, the set of layer-specific molding matrices may comprise layer-specific molding matrices configured for casting layers of teeth of the mandibular dental arch as well as layer-specific molding matrices configured for casting layers of teeth of the maxillary dental arch. The layer-specific molding matrices configured for casting layers of teeth of the mandibular dental arch may be configured to be arranged on the respective teeth of the mandibular dental arch. The layer-specific molding matrices configured for casting layers of teeth of the maxillary dental arch may be configured to be arranged on the respective teeth of the maxillary dental arch.

For example, the layer-specific molding matrices of the set of layer-specific molding matrices may be configured for simultaneously casting layers of teeth of the mandibular dental arch as well as the maxillary dental arch. Such layer-specific molding matrices may be configured to be arranged simultaneously of teeth of the mandibular dental arch as well as on teeth of the maxillary dental arch.

For example, the set of teeth comprises one or more natural teeth. For example, the set of teeth is a set of natural teeth. Examples may have the beneficial effect, that the layer-specific molding matrices of the set of layer-specific molding matrices may be configured for reconstructing layer-by-layer one or more natural teeth.

For example, the set of teeth comprises one or more artificial teeth. Examples may have the beneficial effect, that the layer-specific molding matrices of the set of layer-specific molding matrices may be configured for reconstructing layer-by-layer one or more artificial teeth.

The set of layer-specific molding matrices may be configured for generating multilayer reconstruction of the one or more teeth of the set of teeth in the patient's oral. The multilayer reconstruction generated using the set of layer-specific molding matrices may comprise one or more of the following: a veneer, a crown, an inly, an onlay, an overlay.

A crown is a dental restoration element in form of a dental cap that completely caps or encircles a tooth or dental implant. A crown may, e.g., be required when a large cavity threatens the health of a tooth. A crown may be bonded to the tooth prepared for receiving the crown using a bonding material, e.g., a dental cement. A crown may be made from various materials, which may be fabricated using indirect methods, i.e., outside the patient's oral cavity. Crowns may be used to improve strength, to improve appearance of teeth and/or to halt deterioration.

A veneer is a thin shell of tooth-colored materials configured to cover a surface of a tooth, e.g., a front surface. The veneer may be provided in form of a multilayer shell. Direct veneers are directly built-up on a tooth in the patient's oral cavity. are layer of material placed on a tooth, in order to cover one or more surfaces of the tooth. Indirect veneers are manufactured outside of a patient's oral cavity and then arranged on a tooth within the oral cavity. The tooth may be prepared for receiving the veneer. A full veneer crown may, e.g., cover all the coronal tooth surfaces of a tooth, i.e., mesial, distal, vestibular, oral, and occlusal. A laminate veneer may, e.g., cover only a single surface of a tooth.

Inlays, onlays, and overlays are forms of indirect restoration manufactured outside of a patient's oral cavity as a single, solid piece that fits a specific size and shape of a reception prepared within a tooth of the oral cavity. Inlay, onlay, or overlay are partial crowns, which are bonded, e.g., cemented, in place on the prepared tooth.

An inlay is configured to cover an inner, e.g., central, section of an occlusal surface of a tooth. Thus, an inlay may be used to replace an internal part of a damaged tooth and cover part of the occlusal surface of the respective tooth. The inlay is positioned within hard tissues of the tooth, but does not cover a cusp or pointed part of the tooth. In comparison to an inlay, an onlay in addition covers at least one of the cusps of the tooth. In comparison to an onlay, an overlay covers a larger portion of the occlusal surface of the tooth extending beyond the cusps.

The set of layer-specific molding matrices may be configured for generating on or more of the following: an approximal layer, e.g., a mesial layer or a distal layer, a vestibular layer, e.g., a labial layer or a buccal layer, an oral layer, e.g., a lingual layer or a palatal layer, an occlusal layer, an incisal layer.

The set of layer-specific molding matrices may be configured for generating on or more of the following: an enamel layer, a dentin layer.

The one or more teeth of the set of teeth in the patient's oral for the reconstruction of which the set of layer-specific molding matrices is configured may comprise anterior teeth and/or posterior teeth of the patient. The one or more teeth may, e.g., comprise maxillary and/or mandibular teeth. The one or more teeth may, e.g., comprise one or more of the following: incisors, canines, premolars and/or molars.

In another aspect, the invention relates to a computer program product for providing a set of layer-specific molding matrices for reconstructing layer-by-layer one or more teeth of a set of teeth in a patient's oral cavity. The set of layer-specific molding matrices comprises two or more layer-specific molding matrices. Each of the layer-specific molding matrices is configured for being arranged on the set of teeth and for casting a different layer of the one or more teeth to be reconstructed with a layer-specific reconstruction material inserted into the respective layer-specific molding matrix. The respective layer-specific molding matrix defines a 3D geometric form of the respective layer being casted.

The computer program product comprises a computer readable storage medium. The computer readable storage medium has program instructions embodied therewith. The program instructions are executable by a processor of a computer device to cause the computer device to provide a 3D digital teeth model of the set of teeth in the patient's oral cavity comprising the one or more teeth to be reconstructed. Using the 3D digital teeth model an ordered set of 3D digital layer-specific reconstruction models is generated. Each of the 3D digital layer-specific reconstruction models according to the order adds another one of the layers to be reconstructed to the 3D digital teeth model. Using the ordered set of 3D digital layer-specific reconstruction models an ordered set of 3D digital layer-specific molding matrices is generated. Each of the 3D digital layer-specific molding matrices is a negative of one of the 3D digital layer-specific reconstruction models. The ordered set of 3D digital layer-specific molding matrices are provided as a set of templates for manufacturing the set of layer-specific molding matrices.

The program instructions provided by the computer program product may be configured for causing the computer device to execute any of the aforementioned methods for providing a set of layer-specific molding matrices.

The program instructions provided by the computer program product may, e.g., be further configured for causing the computer device to generate using the 3D digital teeth model the ordered set of 3D digital layer-specific reconstruction models. The ordered set of 3D digital layer-specific reconstruction models is used for generating the ordered set of 3D digital layer-specific molding matrices.

In another aspect, the invention relates to a computer device for providing a set of layer-specific molding matrices for reconstructing layer-by-layer one or more teeth of a set of teeth in a patient's oral cavity. The set of layer-specific molding matrices comprises two or more layer-specific molding matrices. Each of the layer-specific molding matrices is configured for being arranged on the set of teeth and for casting a different layer of the one or more teeth to be reconstructed with a layer-specific reconstruction material inserted into the respective layer-specific molding matrix. The respective layer-specific molding matrix defines a 3D geometric form of the respective layer being casted.

The computer device comprises a processor and a memory. The memory stores program instructions executable by the processor. Execution of the program instructions by the processor causes the computer device to provide a 3D digital teeth model of the set of teeth in the patient's oral cavity comprising the one or more teeth to be reconstructed. Using the 3D digital teeth model an ordered set of 3D digital layer-specific reconstruction models is generated. Each of the 3D digital layer-specific reconstruction models according to the order adds another one of the layers to be reconstructed to the 3D digital teeth model. Using the ordered set of 3D digital layer-specific reconstruction models an ordered set of 3D digital layer-specific molding matrices is generated. Each of the 3D digital layer-specific molding matrices is a negative of one of the 3D digital layer-specific reconstruction models. The ordered set of 3D digital layer-specific molding matrices are provided as a set of templates for manufacturing the set of layer-specific molding matrices.

The computer device may be configured for executing any of the aforementioned methods for providing a set of layer-specific molding matrices.

The computer device may, e.g., be further configured to generate using the 3D digital teeth model the ordered set of 3D digital layer-specific reconstruction models. The ordered set of 3D digital layer-specific reconstruction models is used for generating the ordered set of 3D digital layer-specific molding matrices.

In another aspect, the invention relates to a manufacturing system comprising the computer device for providing a set of layer-specific molding matrices for reconstructing layer-by-layer one or more teeth of a set of teeth in a patient's oral cavity. The manufacturing system further comprises a manufacturing device configured to manufacture the set of layer-specific molding matrices. Execution of the program instructions by the processor further causes the computer device to control the manufacturing device to manufacture the set of layer-specific molding matrices using the ordered set of 3D digital layer-specific molding matrices as templates. Each of the manufactured layer-specific molding matrices of the set of layer-specific molding matrices is a physical copy of one of the templates.

The manufacturing system may be configured for manufacturing any of the aforementioned examples of a set of layer-specific molding matrices.

For example, the manufacturing device is one of the following: a machining device, a 3D printing device.

In another aspect, the invention relates to a set of layer-specific molding matrices for reconstructing layer-by-layer one or more teeth of a set of teeth in a patient's oral cavity. The set of layer-specific molding matrices comprises two or more layer-specific molding matrices. Each of the layer-specific molding matrices is configured for being arranged on the set of teeth and for casting a different layer of the one or more teeth to be reconstructed with a layer-specific reconstruction material inserted into the respective layer-specific molding matrix. The respective layer-specific molding matrix defines a 3D geometric form of the respective layer being casted.

The set of layer-specific molding matrices may, e.g., be a set of machined, 3D printed and/or casted layer-specific molding matrices.

The set of layer-specific molding matrices may be any of the aforementioned examples of a set of layer-specific molding matrices. The set of layer-specific molding matrices may be manufactured using any of the aforementioned examples of a method for manufacturing a set of layer-specific molding matrices.

The above-described examples and embodiments may be combined freely as long as the combinations are not mutually exclusive.

In the following, embodiments of the invention are described in greater detail in which FIG. 1 shows an exemplary first 3D digital layer-specific molding matrix;

Figure 7C:
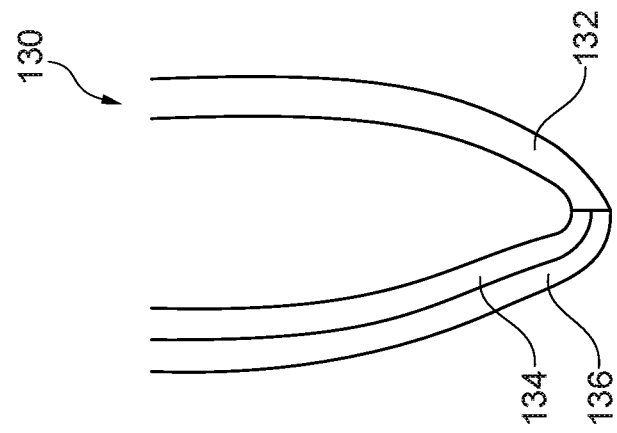
Figure 7B:
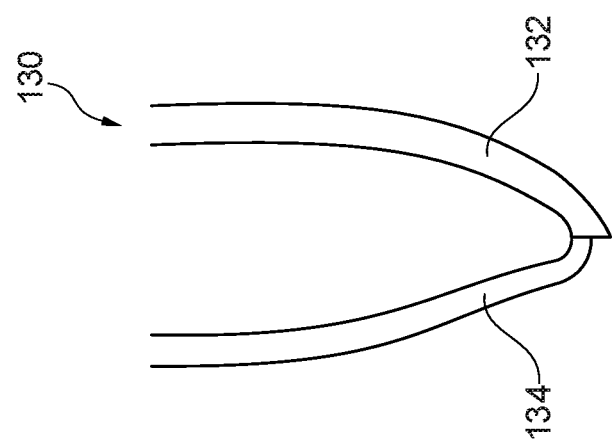
Figure 7A:
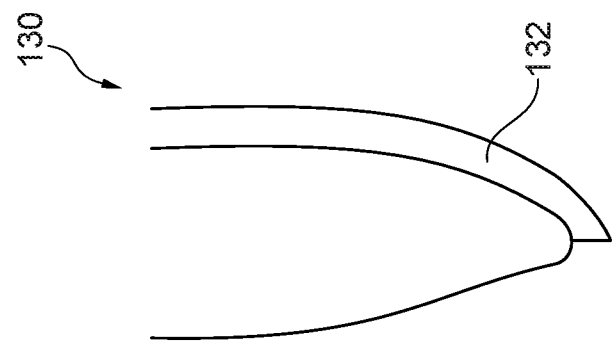
Figure 8:
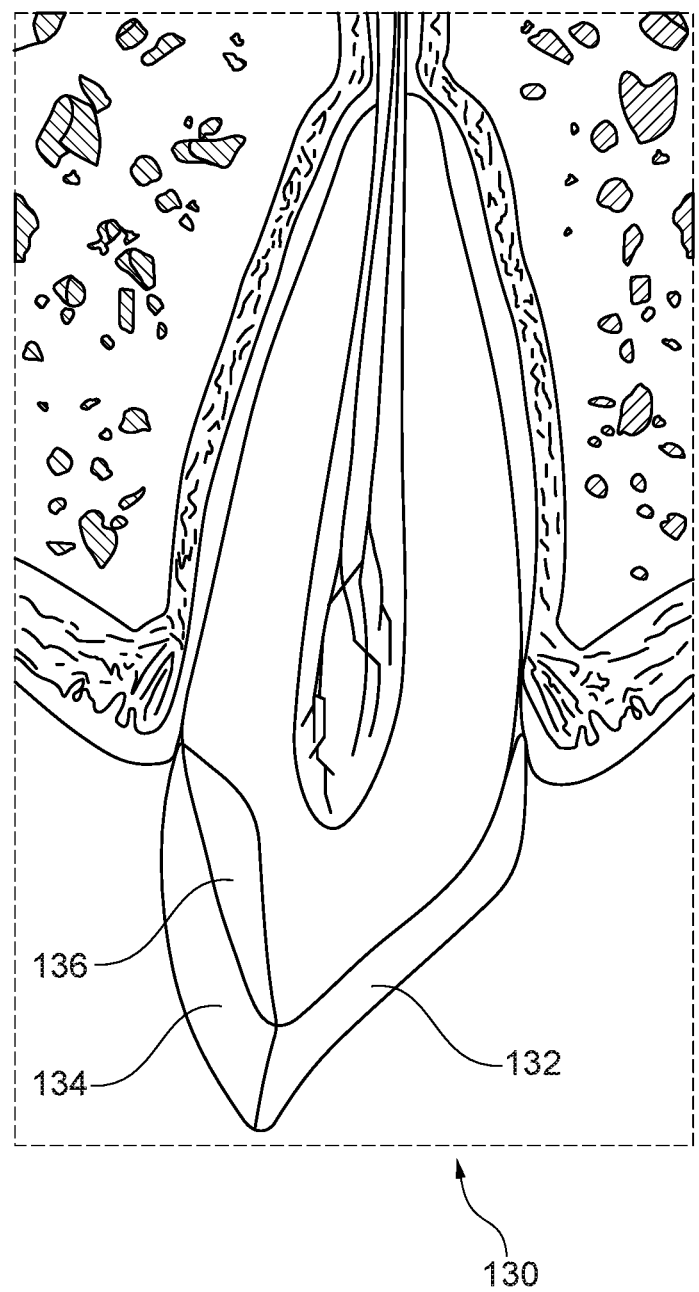
Figure 9:
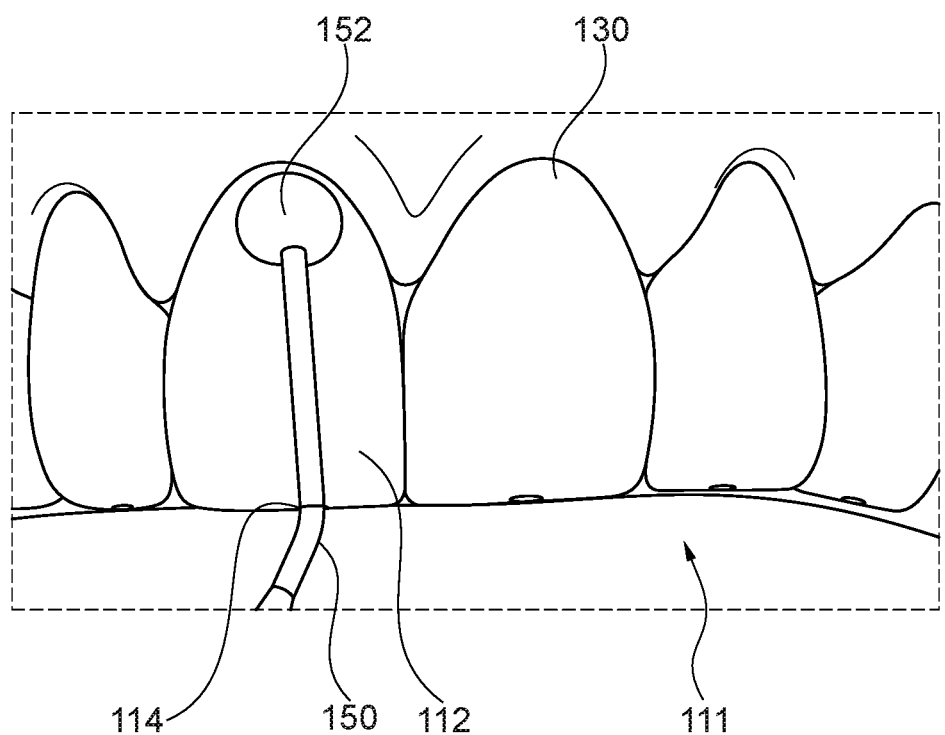
Figure 10:
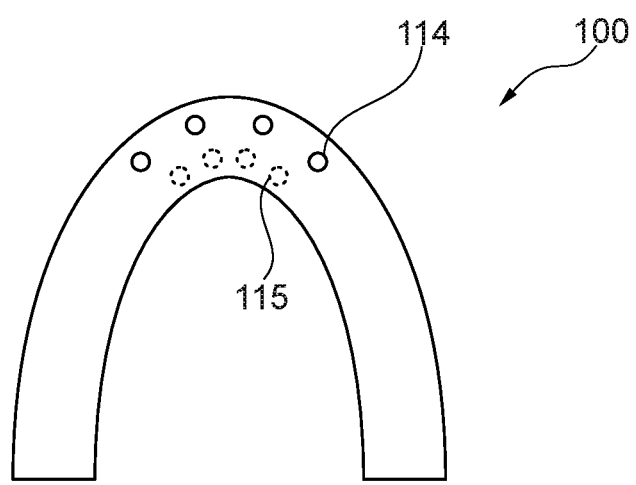
Figure 11:
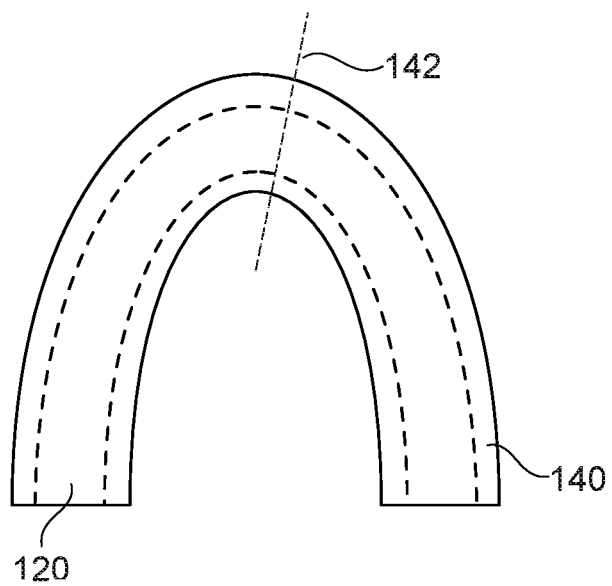
Figure 12:
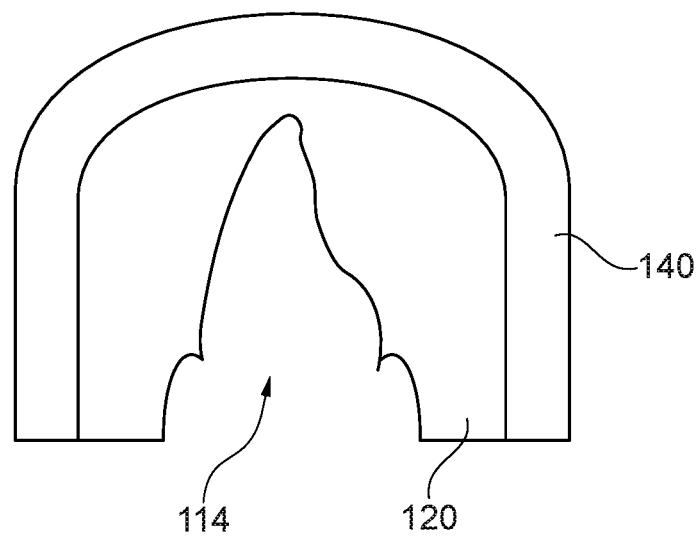
Figure 13:
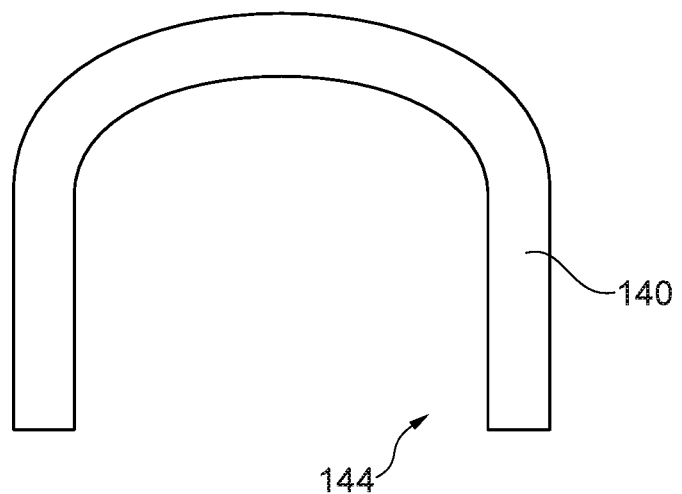
Figure 14:
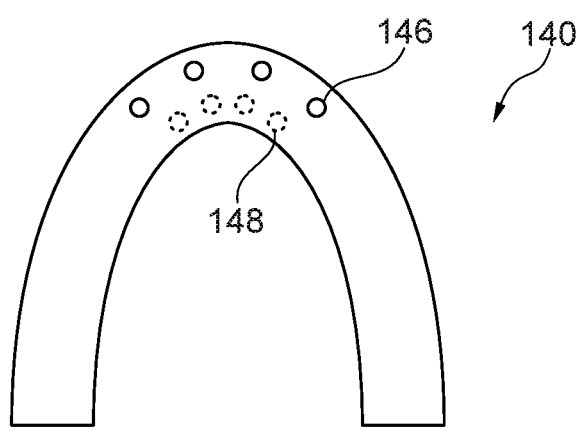
Figure 15:
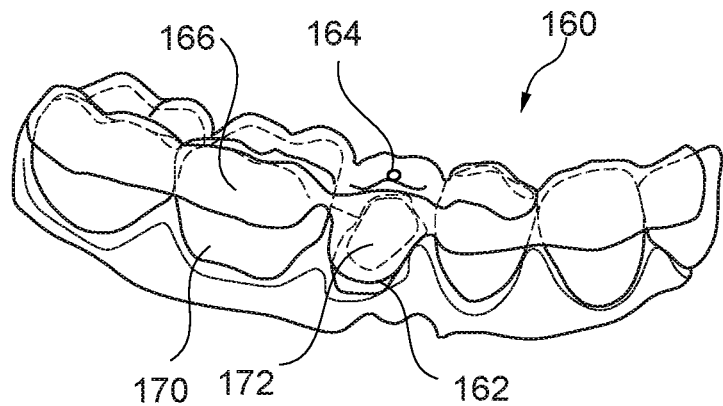
Figure 16:
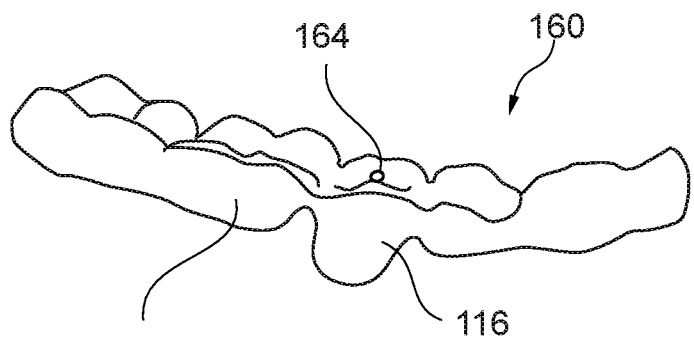
Figure 17:
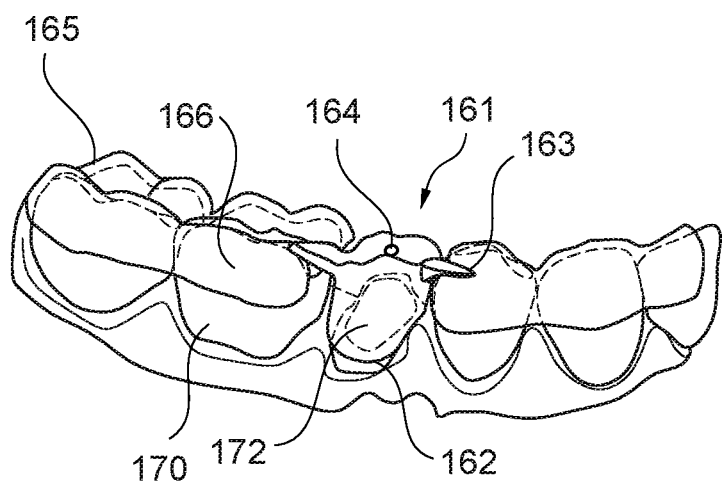
Figure 18:
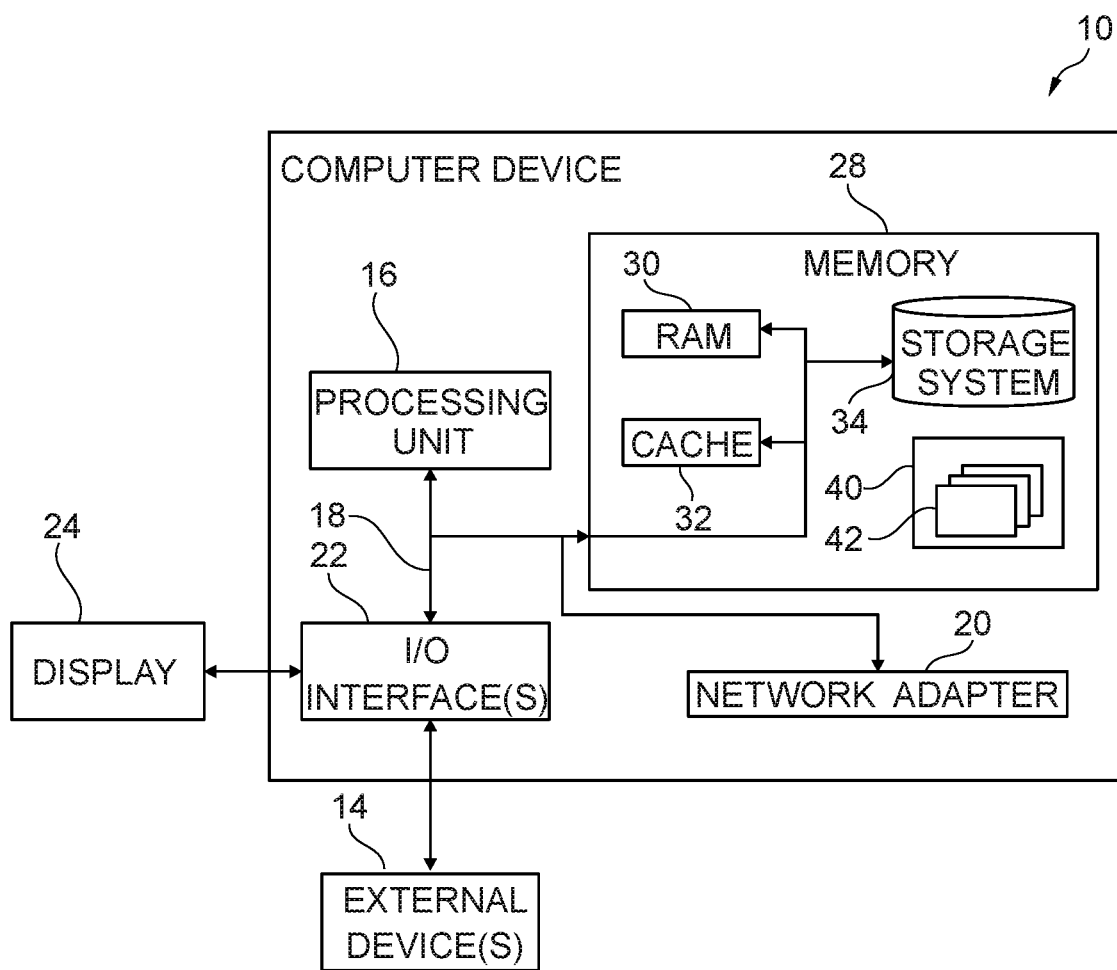
Figure 19:
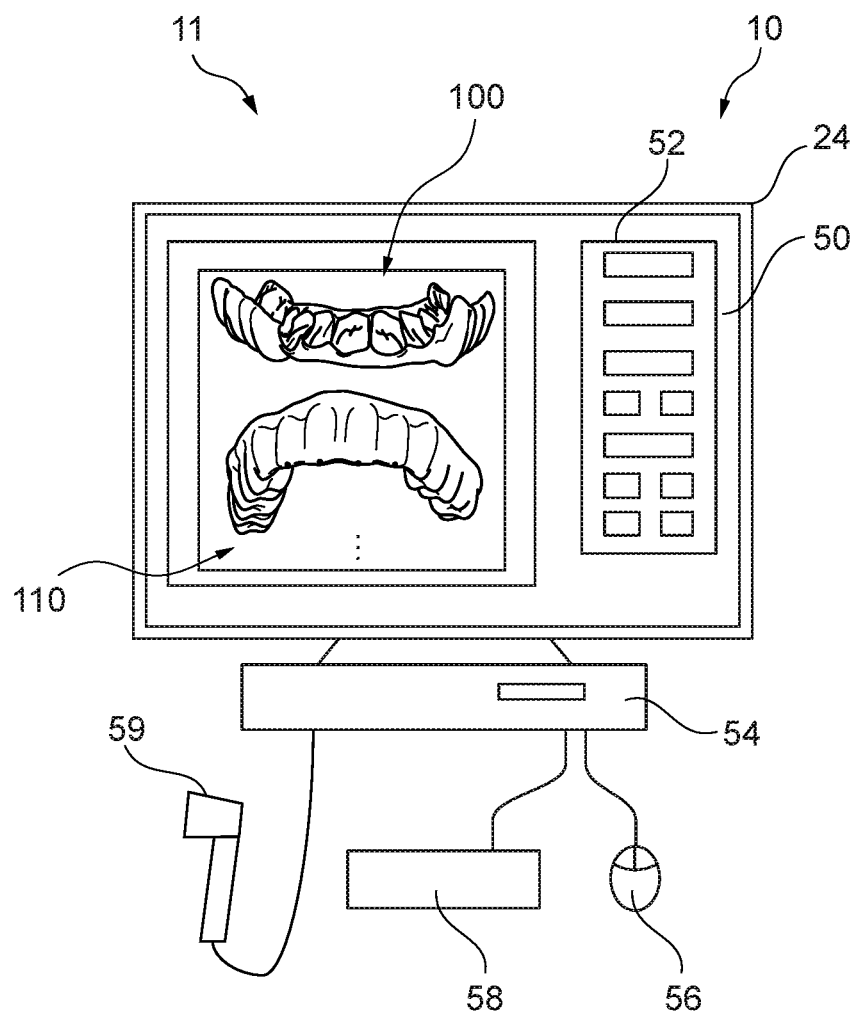
Figure 20:
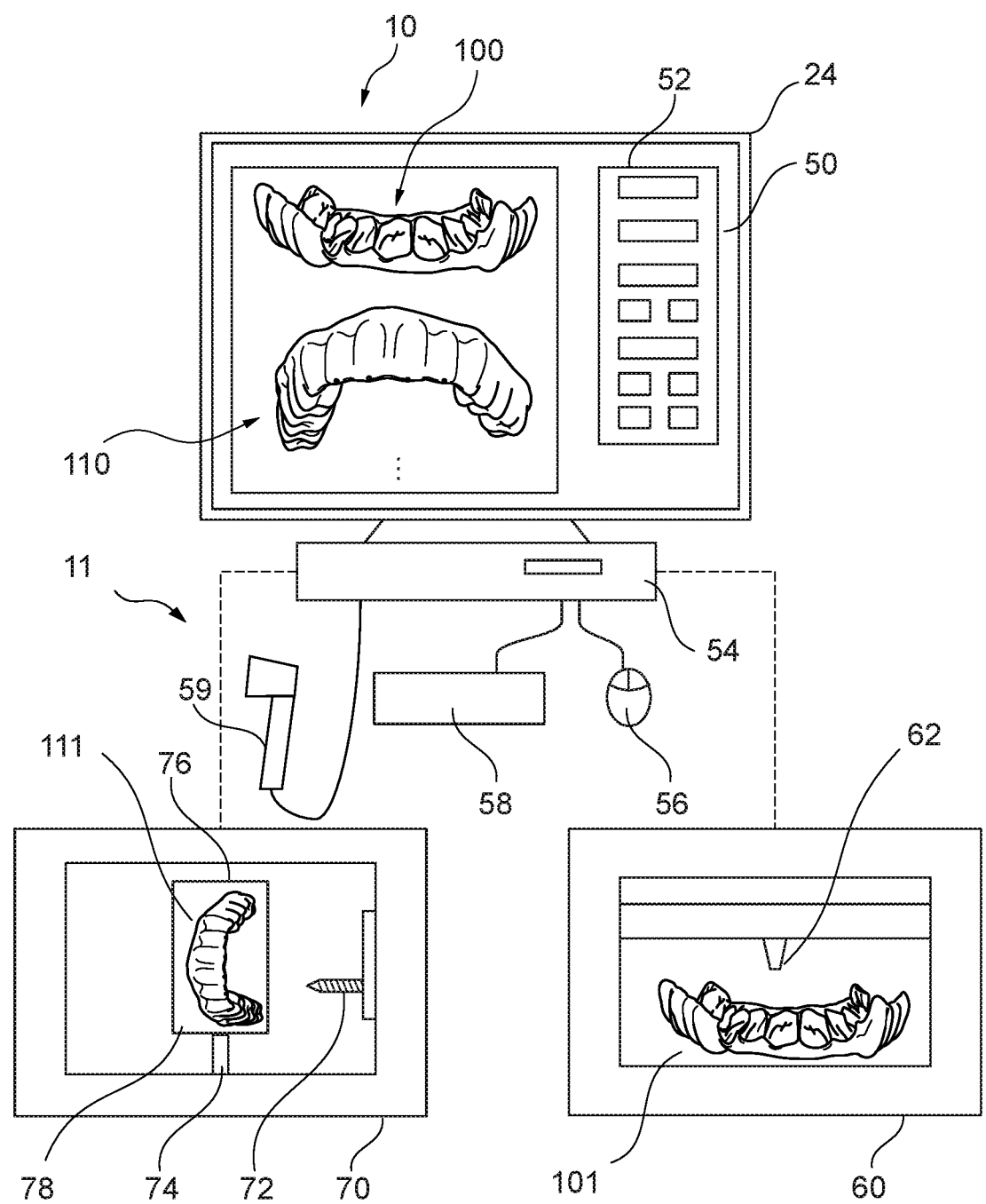
Figure 21:
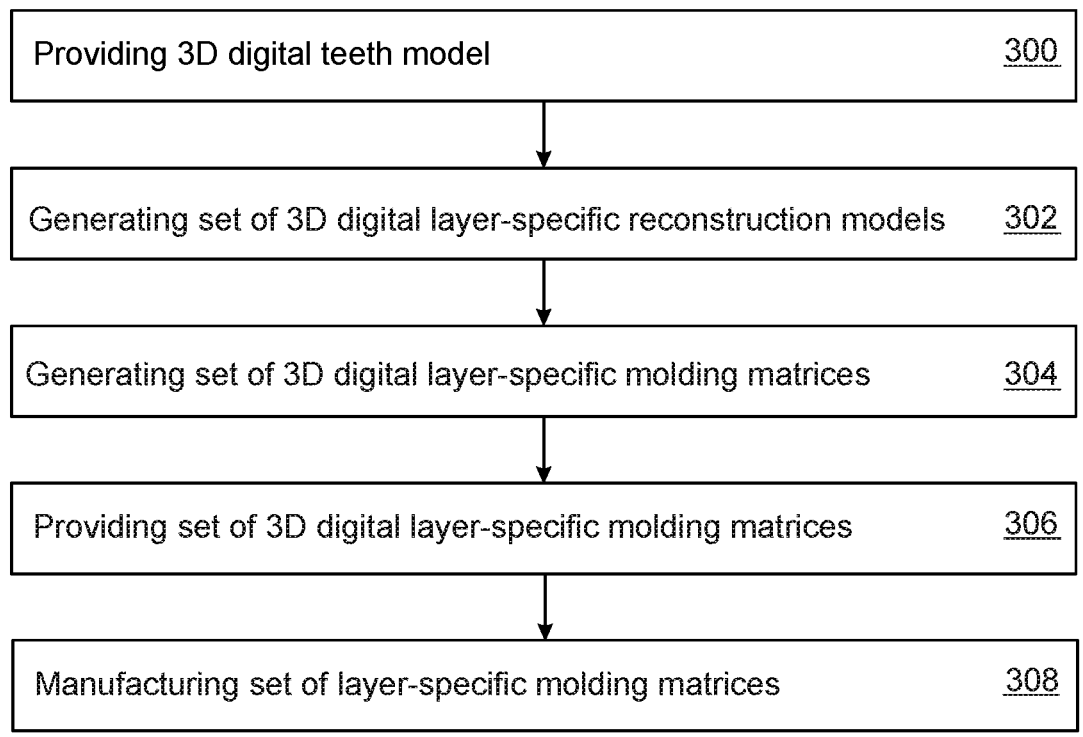
Figure 22:
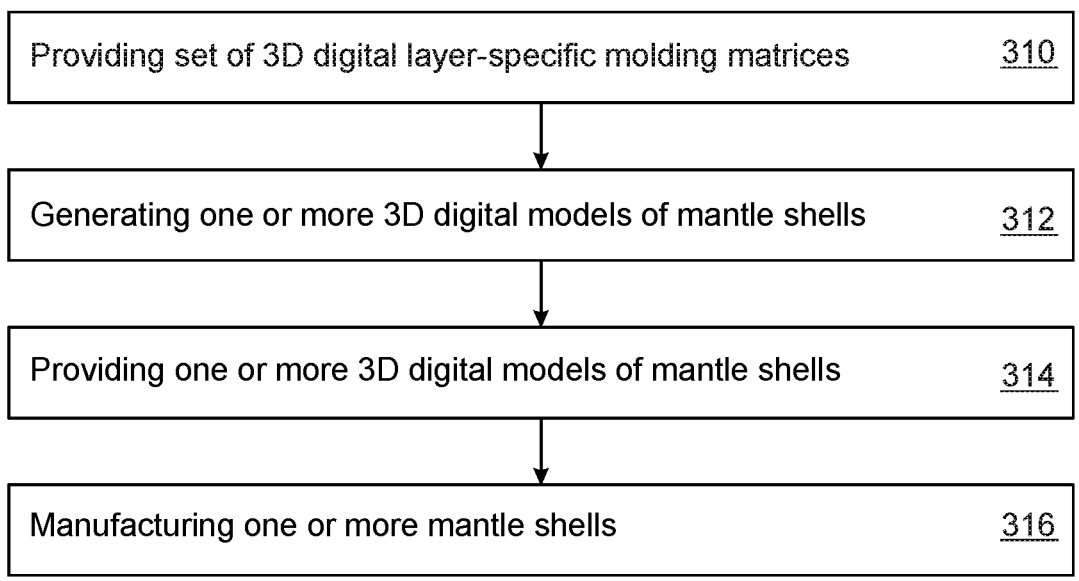
Figure 23:
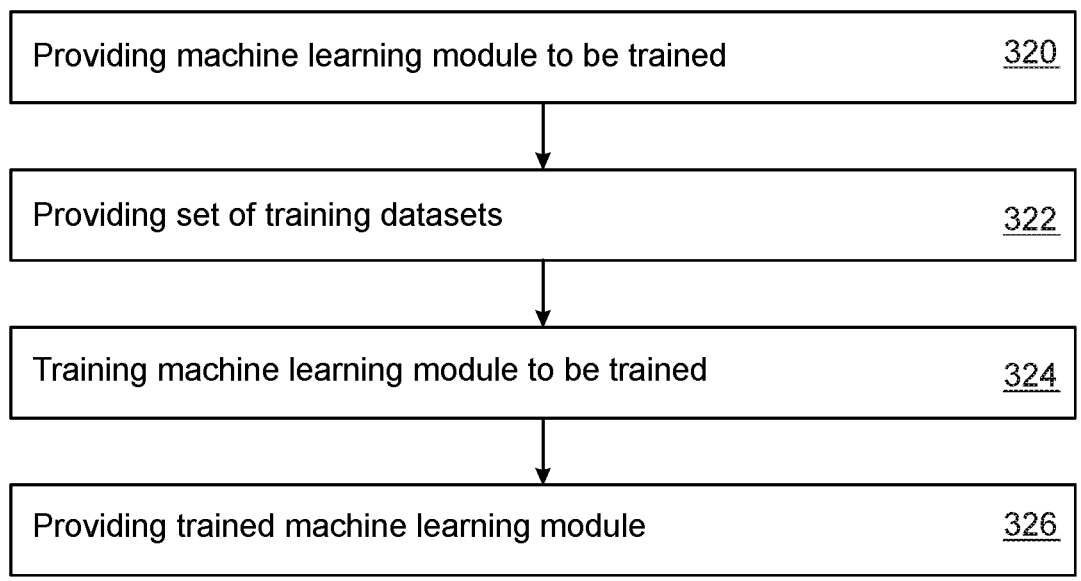
Figure 24:
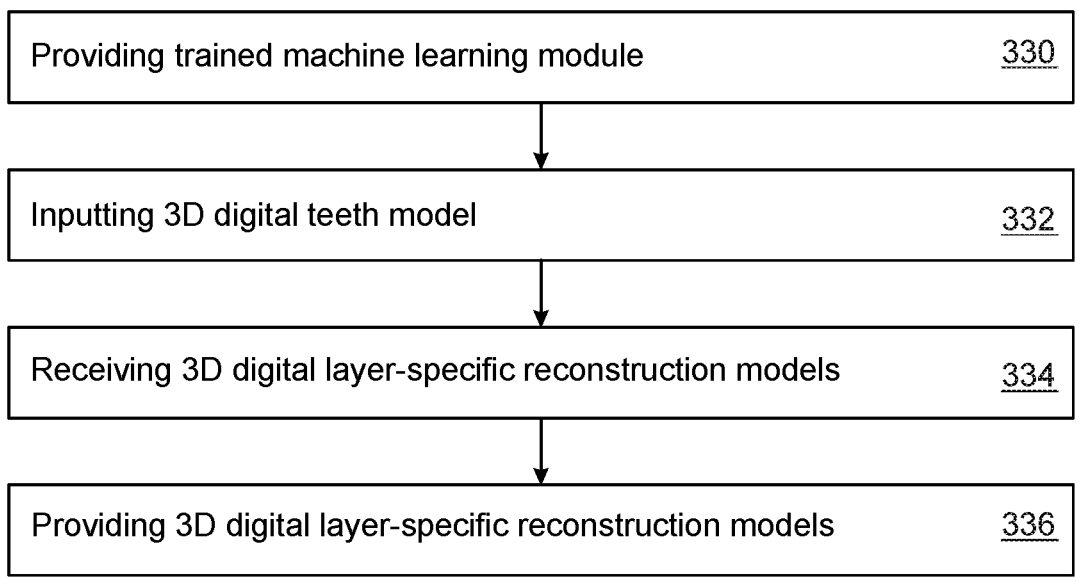
Figure 25:
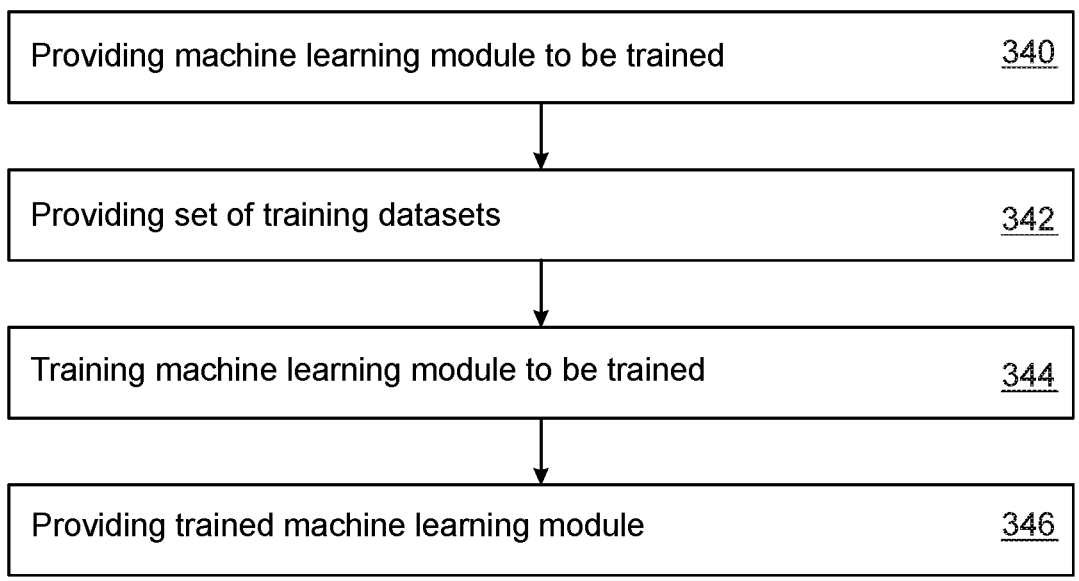
Figure 26:
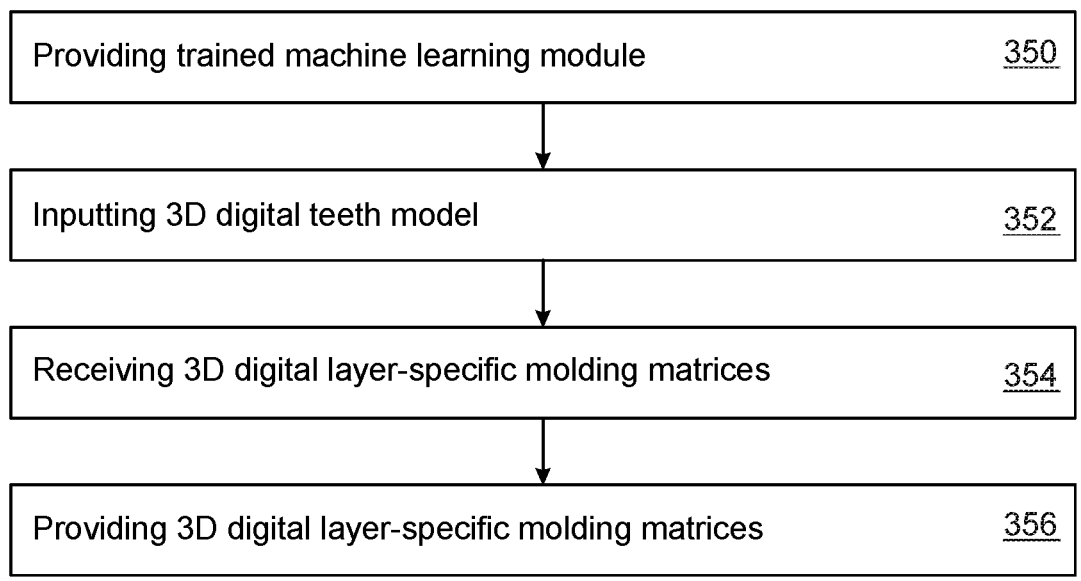

FIG. 7A-C show steps of an exemplary layer-by-layer reconstruction of a tooth;

FIG. 8 shows an exemplary cross-sectional view of a tooth with three reconstructed layers;

FIG. 9 shows an exemplary insertion of a layer-specific casting material in a layer-specific molding matrix;

FIG. 10 shows an exemplary layer-specific molding matrix with injection and venting channels;

FIG. 11 shows an exemplary mantle shell;

FIG. 12 shows a cross-sectional view of a sectional plane through an exemplary mantle shell model on an exemplary layer-specific molding matrix;

FIG. 13 shows a cross-sectional view of a sectional plane through an exemplary mantle shell;

FIG. 14 shows an exemplary mantle shell model with injection and venting channels;

FIG. 15 shows an exemplary 3D digital layer-specific molding matrix arranged on a 3D digital teeth model;

FIG. 16 shows the exemplary 3D digital layer-specific molding matrix of FIG. 15;

FIG. 17 shows an exemplary 3D digital layer-specific molding matrix in form of an exchangeable molding element;

FIG. 18 shows an exemplary computer device for providing templates for a set of layer-specific molding matrices;

FIG. 19 shows an exemplary computer device for providing templates for a set of layer-specific molding matrices;

FIG. 20 shows an exemplary manufacturing system for manufacturing a set of layer-specific molding matrices;

FIG. 21 shows a flowchart illustrating an exemplary method for manufacturing a set of layer-specific molding matrices;

FIG. 22 shows a flowchart illustrating an exemplary method for manufacturing a mantle shell;

FIG. 23 shows a flowchart illustrating an exemplary method for training a machine learning module to be trained;

FIG. 24 shows a flowchart illustrating an exemplary method for using a trained machine learning module;

FIG. 25 shows a flowchart illustrating an exemplary method for training a machine learning module to be trained; and FIG. 26 shows a flowchart illustrating an exemplary method for using a trained machine learning module.

In the following similar features are denoted by the same reference numerals.

Figure 1:
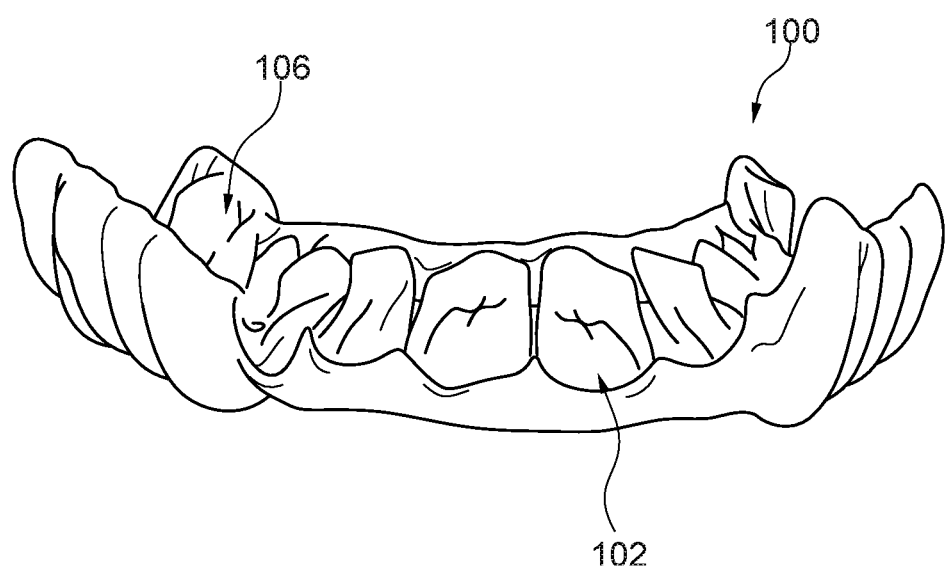

FIG. 1 shows a first exemplary 3D digital layer-specific molding matrix 100. The 3D digital layer-specific molding matrix 100 may be used as a template for manufacturing a first layer-specific molding matrix. Such a first layer-specific molding matrix may be configured for reconstructing a layer of one or more teeth in a patient's oral cavity. The 3D digital layer-specific molding matrix 100 shown in FIG. 1 is, e.g., configured for reconstructing a palatine enamel layer of the teeth in the patient's oral cavity. This layer may, e.g., further define a cutback structure of the teeth visibly through the further layers to be reconstructed. The 3D digital layer-specific molding matrix 100 comprises one or more recesses 102. The recesses 102 are configured to receive the teeth of the patient's oral cavity on which the layer is to be reconstructed using the layer-specific molding matrix defined by the 3D digital layer-specific molding matrix 100. Each of the recesses 102 has a 3D geometric form, which is a negative of the tooth of the patient's oral cavity to be received by the respective recess 102 in combination with the layer to be reconstructed by the respective layer-specific molding matrix. In the present case, the additional layer is a palatal enamel layer. When the 3D digital layer-specific molding matrix 100 is arranged on a 3D digital layer-specific reconstruction model defining a 3D geometric form of the teeth on which the additional layer is to be reconstructed, a hollow section remains within each of the recesses 102 defining a 3D geometric form of the additional layer to be reconstructed. When a layer-specific molding matrix manufactured using the 3D digital layer-specific molding matrix 100 is arranged on teeth in the patient's oral cavity, on which the additional layer is to be reconstructed, a hollow section remains within each of the recesses 102 defining a 3D geometric form of the additional layer to be reconstructed.

Furthermore, the 3D digital layer-specific molding matrix 100 may comprise further recesses 106 for fixating the layer-specific molding matrix defined by the 3D digital layer-specific molding matrix 100 on one or more teeth in the patient's oral cavity. These recesses 106 may have 3D geometric forms, which are negatives of 3D geometric forms of the teeth to be received by the respective recesses 106.

The 3D digital layer-specific molding matrix 100 may furthermore comprise one or more injection channels configured to insert layer-specific reconstruction material in each of the recesses 102, e.g., by injection. In addition, the 3D digital layer-specific molding matrix 100 may further comprise one or more venting channels configured for letting out air, when the layer-specific reconstruction material is into the recesses 102 defined by the 3D digital layer-specific molding matrix 100. The injection channels and/or venting channels may, e.g., comprise mouths arranged on an occlusal face of the 3D digital layer-specific molding matrix 100.

The 3D digital layer-specific molding matrix 100 shown in FIG. 1 is one 3D digital layer-specific molding matrix of a set of 3D digital layer-specific molding matrices. The set of 3D digital layer-specific molding matrices comprises a plurality of 3D digital layer-specific molding matrices, e.g., two, three or four 3D digital layer-specific molding matrices. Each of the 3D digital layer-specific molding matrices defines a layer-specific molding matrix and may be used as a template to manufacture the respective layer-specific molding matrix. Such 3D digital layer-specific molding matrices may, e.g., be manufactured using a CAD/CAM method, like machining or 3D printing. Furthermore, such 3D digital layer-specific molding matrices may be manufactured using casting. A casting matrix for the casting may, e.g., be manufactured using a CAD/CAM method. The resulting set of layer-specific molding matrices comprises a plurality of layer-specific molding matrices for reconstructing layer-by-layer one or more teeth of a set of teeth in a patient's oral cavity. Each of the layer-specific molding matrices is configured for being arranged on the set of teeth and for casting a different layer of the one or more teeth to be reconstructed with a layer-specific reconstruction material inserted into the respective layer-specific molding matrix. The respective layer-specific molding matrix defines a 3D geometric form of the respective layer being casted.

For generating the 3D digital layer-specific molding matrix 100, a 3D digital teeth model of the set of teeth in the patient's oral cavity may be provided comprising the one or more teeth to be reconstructed. Using the 3D digital teeth model an ordered set of 3D digital layer-specific reconstruction models may be generated. Each of the 3D digital layer-specific reconstruction models according to the order adds another one of the layers to be reconstructed to the 3D digital teeth model. Thus, the first 3D digital layer-specific reconstruction model according to the order may correspond to the 3D digital teeth model with a first reconstructed layer added to one or more of the teeth of the 3D digital teeth model. The second 3D digital layer-specific reconstruction model according to the order may correspond to the first 3D digital layer-specific reconstruction model with a second reconstructed layer added to one or more of the teeth of the first 3D digital layer-specific and so on.

Using the ordered set of 3D digital layer-specific reconstruction models, the ordered set of 3D digital layer-specific molding matrices comprising the 3D digital layer-specific molding matrix 100 may be generated. The 3D digital layer-specific molding matrix 100 is a negative of one of the 3D digital layer-specific reconstruction models.

The resulting set of 3D digital layer-specific molding matrices with the 3D digital layer-specific molding matrix 100 may be used to manufacture a set of corresponding layer-specific molding matrices. These layer-specific molding matrices nay be used to reconstruct following the order layer-by-layer the one or more teeth to be reconstructed. The reconstructed layers may be shaped and colored to mimic the multilayer structure of the patient's natural teeth.

The 3D digital teeth model may be part of a 3D digital tissue model comprising hard tissue, like teeth, as well as soft tissue, like gingiva, of the patient's oral cavity. The 3D digital teeth model and/or the 3D digital tissue model may, e.g., be provided using scan data of the patient's oral cavity. For example, the patient's tissue in the oral cavity may be scanned using a scanner, e.g., an optical scanner. The achieved scan data may be used to generate and provide the 3D digital teeth model. Alternatively, an impression of the patient's tissue in the oral cavity, i.e., a negative imprint of hard and/or soft tissue may be taken. Either this impression may be scanned, e.g., using an optical scanner or the negative imprint provided by the impression may be used to generate a positive reproduction of the respective tissue of the patient, i.e., a 3D physical tissue model or cast, which is scanned, e.g., by the optical scanner to provide the scan data used to generate the 3D digital teeth model or 3D digital tissue model.

Figure 2:
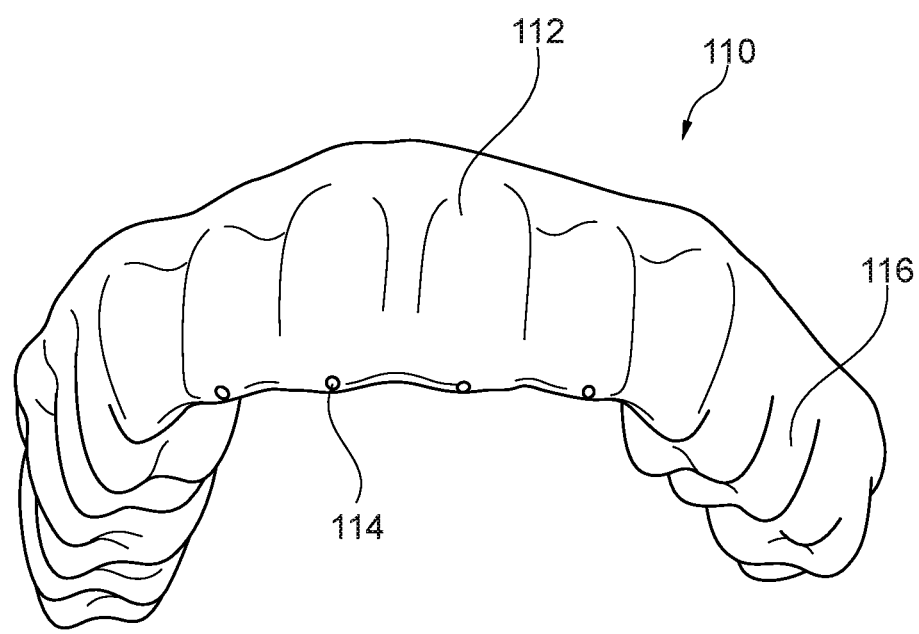
FIG. 2 shows an exemplary second 3D digital layer-specific molding matrix.

FIG. 2 shows a second exemplary 3D digital layer-specific molding matrix 110. The 3D digital layer-specific molding matrix 110 may be used as a template for manufacturing a second layer-specific molding matrix. Such a layer-specific molding matrix may be configured for reconstructing a second layer of the teeth in a patient's oral cavity. The 3D digital layer-specific molding matrix 110 shown in FIG. 2 is configured for reconstructing a labial dentin layer of the teeth in the patient's oral cavity. The 3D digital layer-specific molding matrix 110 comprises one or more recesses 112. The recesses 112 are configured to receive the teeth of the patient's oral cavity on which the layer is to be reconstructed using the layer-specific molding matrix defined by the 3D digital layer-specific molding matrix 110. Each of the recesses 112 has a 3D geometric form, which is a negative of the tooth of the patient's oral cavity to be received by the respective recess 112 in combination with the layer to be reconstructed by the respective layer-specific molding matrix. In the present case, the additional layer is a labial dentin layer. When the 3D digital layer-specific molding matrix 110 is arranged on a 3D digital layer-specific reconstruction model defining a 3D geometric form of the teeth on which the additional layer is to be reconstructed, a hollow section remains within each of the recesses 102 defining a 3D geometric form of the additional layer to be reconstructed. When a layer-specific molding matrix manufactured using the 3D digital layer-specific molding matrix 110 is arranged on teeth in the patient's oral cavity, on which the additional layer is to be reconstructed, a hollow section remains within each of the recesses 102 defining a 3D geometric form of the additional layer to be reconstructed.

Furthermore, the 3D digital layer-specific molding matrix 110 may comprise further recesses 116 for fixating the layer-specific molding matrix defined by the 3D digital layer-specific molding matrix 110 on one or more teeth in the patient's oral cavity. These recesses 116 may have 3D geometric forms, which are negatives of 3D geometric forms of the teeth to be received by the respective recesses 116.

The 3D digital layer-specific molding matrix 110 may furthermore comprise one or more injection channels 114 configured to insert layer-specific reconstruction material in each of the recesses 112, e.g., by injection. The injection channels 114 may, e.g., comprise mouths arranged on an occlusal face of the 3D digital layer-specific molding matrix 110. In addition, the 3D digital layer-specific molding matrix 110 may further comprise one or more venting channels configured for letting out air, when the layer-specific reconstruction material is into the recesses 112 defined by the 3D digital layer-specific molding matrix 110. The venting channels may, e.g., comprise mouths arranged on an occlusal face of the 3D digital layer-specific molding matrix 110.

Like the 3D digital layer-specific molding matrix 100 shown in FIG. 1, the 3D digital layer-specific molding matrix 110 shown in FIG. 2 may be a 3D digital layer-specific molding matrix of a set of 3D digital layer-specific molding matrices, e.g., a second 3D digital layer-specific molding matrix according to an order of the set. The 3D digital layer-specific molding matrix 110 may be used to manufacture a layer-specific molding matrix configured to reconstruct a second layer of the teeth in the patient's oral cavity.

Figure 3:
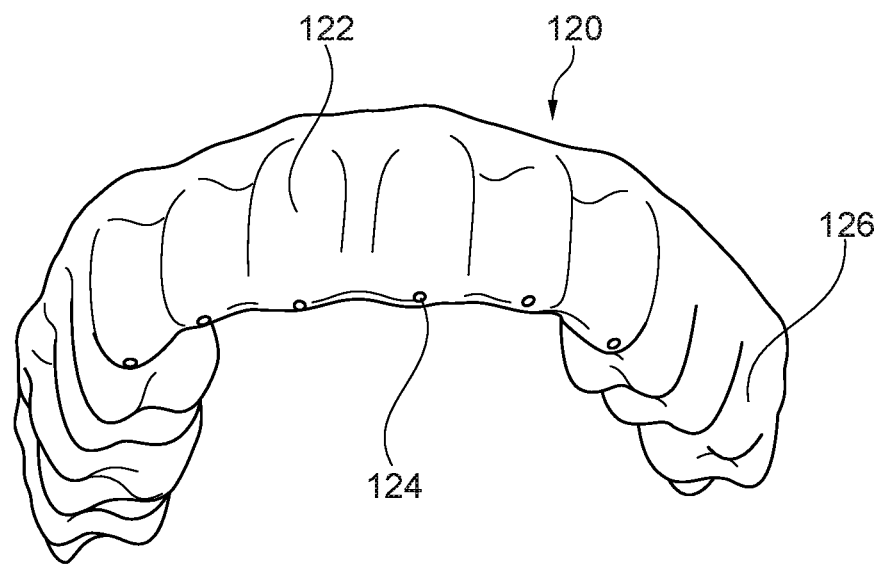
FIG. 3 shows an exemplary third 3D digital layer-specific molding matrix.

FIG. 3 shows a third exemplary 3D digital layer-specific molding matrix 120. The 3D digital layer-specific molding matrix 120 may be used as a template for manufacturing a third layer-specific molding matrix. Such a layer-specific molding matrix may be configured for reconstructing a third layer of the teeth in a patient's oral cavity. The 3D digital layer-specific molding matrix 120 shown in FIG. 3 is configured for reconstructing a labial enamel layer of the teeth in the patient's oral cavity. The 3D digital layer-specific molding matrix 120 comprises one or more recesses 122. The recesses 122 are configured to receive the teeth of the patient's oral cavity on which the layer is to be reconstructed using the layer-specific molding matrix defined by the 3D digital layer-specific molding matrix 120. Each of the recesses 122 has a 3D geometric form, which is a negative of the tooth of the patient's oral cavity to be received by the respective recess 122 in combination with the layer to be reconstructed by the respective layer-specific molding matrix. In the present case, the additional layer is a labial enamel layer. When the 3D digital layer-specific molding matrix 120 is arranged on a 3D digital layer-specific reconstruction model defining a 3D geometric form of the teeth on which the additional layer is to be reconstructed, a hollow section remains within each of the recesses 102 defining a 3D geometric form of the additional layer to be reconstructed. When a layer-specific molding matrix manufactured using the 3D digital layer-specific molding matrix 120 is arranged on teeth in the patient's oral cavity, on which the additional layer is to be reconstructed, a hollow section remains within each of the recesses 102 defining a 3D geometric form of the additional layer to be reconstructed.

Furthermore, the 3D digital layer-specific molding matrix 120 may comprise further recesses 126 for fixating the layer-specific molding matrix defined by the 3D digital layer-specific molding matrix 120 on one or more teeth in the patient's oral cavity. These recesses 126 may have 3D geometric forms, which are negatives of 3D geometric forms of the teeth to be received by the respective recesses 126.

The 3D digital layer-specific molding matrix 120 may furthermore comprise one or more injection channels 124 configured to insert layer-specific reconstruction material in each of the recesses 122, e.g., by injection. The injection channels 124 may, e.g., comprise mouths arranged on an occlusal face of the 3D digital layer-specific molding matrix 120. In addition, the 3D digital layer-specific molding matrix 120 may further comprise one or more venting channels configured for letting out air, when the layer-specific reconstruction material is into the recesses 122 defined by the 3D digital layer-specific molding matrix 120. The venting channels may, e.g., comprise mouths arranged on an occlusal face of the 3D digital layer-specific molding matrix 120.

Like the 3D digital layer-specific molding matrix 100 shown in FIG. 1 and the 3D digital layer-specific molding matrix 110 shown in FIG. 2, the 3D digital layer-specific molding matrix 120 shown in FIG. 3 may be a 3D digital layer-specific molding matrix of a set of 3D digital layer-specific molding matrices, e.g., a third 3D digital layer-specific molding matrix according to an order of the set. The 3D digital layer-specific molding matrix 120 may be used to manufacture a layer-specific molding matrix configured to reconstruct a third layer of the teeth in the patient's oral cavity.

Figure 4:
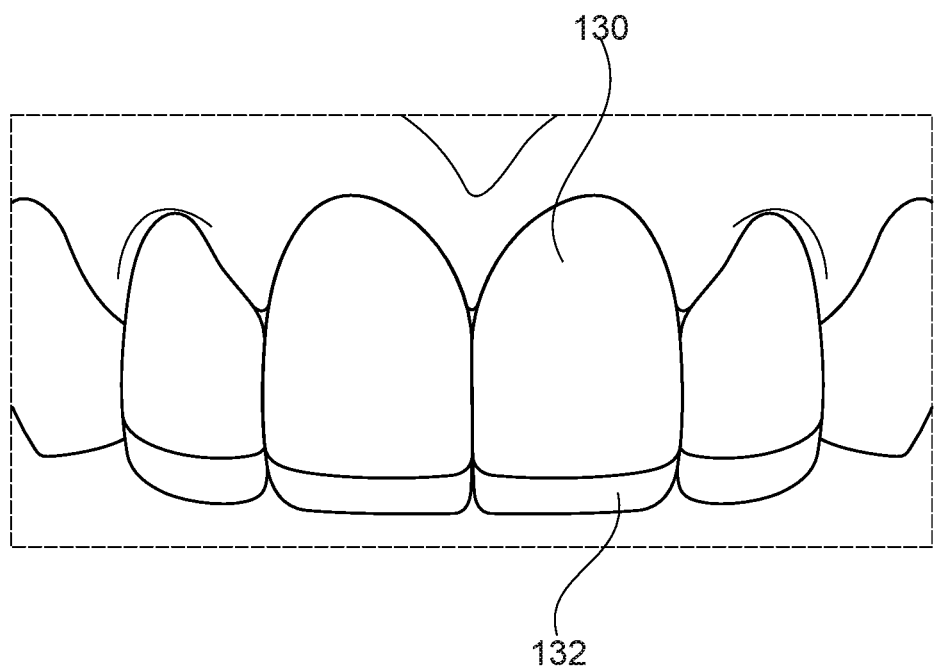
FIG. 4 shows exemplary teeth with a first reconstructed layer.
Figure 5:
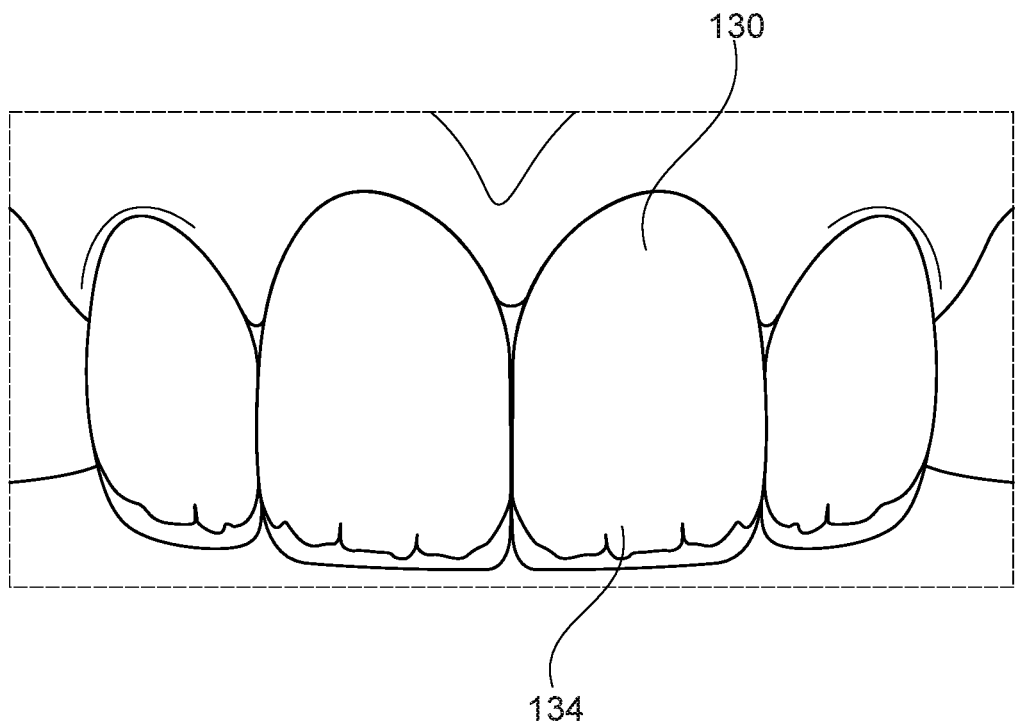
FIG. 5 shows exemplary teeth with a second reconstructed layer.
Figure 6:
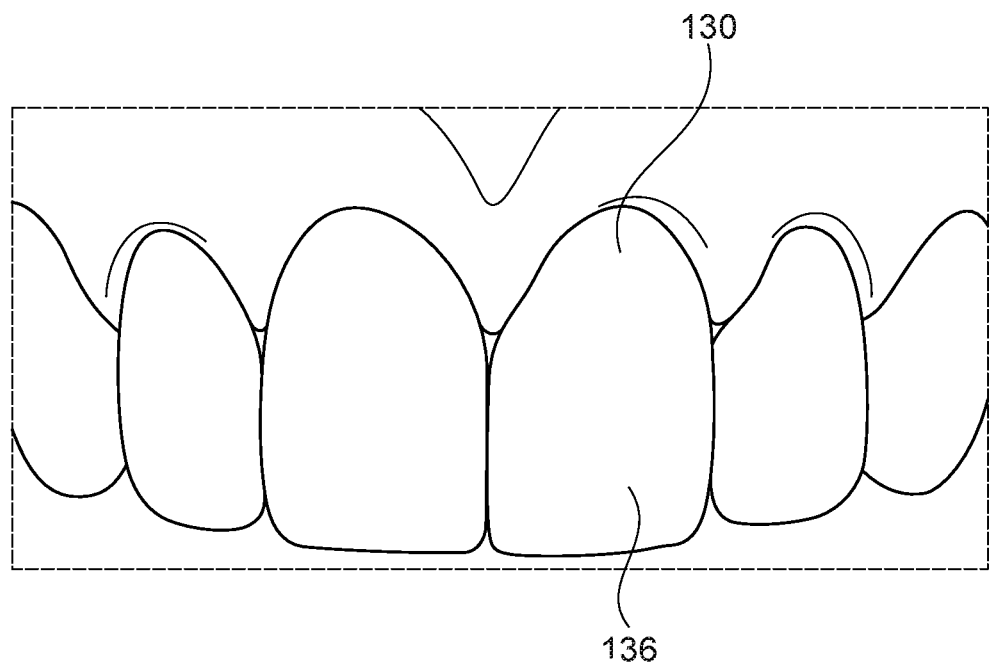
FIG. 6 shows exemplary teeth with a third reconstructed layer.

FIGS. 4, 5, and 6 show different states of a layer-by-layer-reconstruction of teeth 130, e.g., natural teeth, of a patient in the respective patient's oral cavity using a set of layer-specific molding matrices. The set of layer-specific molding matrices may, e.g., comprise three layer-specific molding matrices. The three layer-specific molding matrices of the set of layer-specific molding matrices may be defined by the 3D digital layer-specific molding matrix 100 shown in FIG. 1, the 3D digital layer-specific molding matrix 110 shown in FIG. 2, and the 3D digital layer-specific molding matrix 120 shown in FIG. 3. The layer-specific molding matrix manufactured using the first 3D digital layer-specific molding matrix 100 shown in FIG. 1 may be used to reconstruct on the teeth 130 a first layer 132, e.g., a palatine enamel layer as shown in FIG. 4. The resulting 3D geometry may correspond to the first 3D digital layer-specific reconstruction model used to generate the first 3D digital layer-specific molding matrix 100 shown in FIG. 1.

The layer-specific molding matrix manufactured using the second 3D digital layer-specific molding matrix 110 shown in FIG. 2 may be used to reconstruct on the teeth 130 with the first layer 132 a second layer 134, e.g., a labial dentin layer as shown in FIG. 5. The resulting 3D geometry may correspond to the second 3D digital layer-specific reconstruction model used to generate the second 3D digital layer-specific molding matrix 110 shown in FIG. 2. The layer-specific molding matrix manufactured using the third 3D digital layer-specific molding matrix 120 shown in FIG. 3 may be used to reconstruct on the teeth 130 with the first and second layers 132, 134 a third layer 136, e.g., a labial enamel layer as shown in FIG. 6. The resulting 3D geometry may correspond to the third 3D digital layer-specific reconstruction model used to generate the third 3D digital layer-specific molding matrix 120 shown in FIG. 3.

FIG. 7A, FIGS. 7B, and 7C illustrate steps of an exemplary layer-by-layer reconstruction of one of the teeth 130 of FIG. 4 to FIG. 6. FIG. 7A shows a cross-sectional view of one of the teeth 130 of FIG. 4, FIG. 7B shows a cross-sectional view of one of the teeth 130 of FIG. 5, and FIG. 7C shows a cross-sectional view of one of the teeth 130 of FIG. 6. In FIG. 7A a first layer 132 is reconstructed. The first layer 132 may, e.g., be a palatine enamel layer. The first layer 132 may, e.g., be reconstructed using a first layer-specific molding matrix defined by the first 3D digital layer-specific molding matrix 100 shown in FIG. 1. In FIG. 7B a second layer 134 is reconstructed. The second layer 134 may, e.g., be a labial dentin layer. The second layer 134 may, e.g., be reconstructed using a second layer-specific molding matrix defined by the second 3D digital layer-specific molding matrix 110 shown in FIG. 2. In FIG. 7C a third layer 136 is reconstructed. The third layer 136 may, e.g., be a labial enamel layer. The third layer 136 may, e.g., be reconstructed using a third layer-specific molding matrix defined by the third 3D digital layer-specific molding matrix 120 shown in FIG. 3.

FIG. 8 shows a cross-sectional view of one of the teeth 130 of FIG. 6 with three reconstructed layers 132, 134, 136. The reconstructed tooth 130 shown in FIG. 8 may, e.g., be the result of the exemplary layer-by-layer reconstruction illustrated in FIG. 7A, FIGS. 7B, and 7C. The three reconstructed layers comprise, e.g., a first palatine enamel layer 132, a second labial dentin layer 134, and a third labial enamel layer 136. The three layers 132, 134, 136 are reconstructed layer-by-layer using three layer-specific molding matrices defined by the first 3D digital layer-specific molding matrix 100 shown in FIG. 1, the second 3D digital layer-specific molding matrix 110 shown in FIG. 2, and the third 3D digital layer-specific molding matrix 120 shown in FIG. 3.

FIG. 9 shows an exemplary insertion of a layer-specific casting material 152 in a layer-specific molding matrix 111. The layer-specific molding matrix 111 may, e.g., be a layer-specific molding matrix for reconducting a palatine dentin layer. The layer-specific molding matrix 111 may be defined by the 3D digital layer-specific molding matrix 110 shown in FIG. 2. The layer-specific molding matrix 111 is arranged on the teeth 130 in the patient's oral cavity, such that the teeth to be reconstructed are received in the recesses 112 of the layer-specific molding matrix 111. A nozzle of an insertion device 150 for inserting layer-specific reconstruction material 152 into the remaining hollow section provided within the recess 112 of the layer-specific molding matrix 111 arranged on the teeth 130 to be reconstructed. The nozzle of an insertion device 150 is, e.g., inserted into the recess 112 via an injecting channel 114 of the layer-specific molding matrix 111. The insertion device 150 is used to insert inserting layer-specific reconstruction material 152 into the recess 112 by injection. The inserted layer-specific reconstruction material 152 is chosen to mimic, e.g., in color and in the degree of opacity/translucency the layer to be reconstructed. For example, the layer-specific reconstruction material 152 used for reconstructing the palatine dentin layer may be opaque, while layer-specific reconstruction material reconstructing an enamel layer may, e.g., be translucent.

FIG. 10 shows an exemplary 3D digital layer-specific molding matrix 100, e.g., corresponding to the 3D digital layer-specific molding matrix of FIG. 1. The 3D digital layer-specific molding matrix 100 comprises injection channels 114. Furthermore, the 3D digital layer-specific molding matrix 100 may comprise venting channels 115. The 3D digital layer-specific molding matrix 100 is depicted from its occlusal side. A layer-specific molding matrix manufactured using the 3D digital layer-specific molding matrix 100 as a template may comprise the injection channels 114 and venting channels 115 as well. The injection channels 114 are configured for injecting layer-specific reconstruction material into the recesses of the layer-specific molding matrix defined by the 3D digital layer-specific molding matrix 100. For injecting the layer-specific reconstruction material, an injection device may be used, e.g., a reciprocating pump, like a syringe. The injection channels 114 may each, e.g., comprise a mouth arranged on an occlusal side of the layer-specific molding matrix as shown in FIG. 10. The layer-specific molding matrix may, e.g., comprise an injection channel 114 for each of the recesses receiving a tooth on which a layer is to be reconstructed.

The venting channels 115 may be configured for letting out air form the recesses of the layer-specific molding matrix defined by the 3D digital layer-specific molding matrix 100, when the layer-specific reconstruction material is injected via the injection channels 114 into the recesses. The venting channels 115 may ensure an effective venting of the layer-specific molding matrix, when the layer-specific reconstruction material being injected into the layer-specific molding matrix generates an overpressure within the layer-specific molding matrix relative to the environment of the layer-specific molding matrix.

FIG. 11 shows a 3D digital model of a mantle shell 140 for a layer-specific molding matrix defined by a 3D digital layer-specific molding matrix 120. The 3D digital model of the mantle shell 140 is a negative of an outer 3D geometrical form of the 3D digital layer-specific molding matrix 120. The respective outer 3D geometrical form is defined by outer surface sections configured to come in contact with inner surface sections of the 3D digital model of the mantle shell, when the mantle shell is arranged on the respective digital layer-specific molding matrix. The 3D digital model of the mantle shell 140 may, e.g., define a generic mantle shell, which is configured to be used with every 3D digital layer-specific molding matrix comprised by the set of 3D digital layer-specific molding matrices with the 3D digital layer-specific molding matrix 120. For example, all the 3D digital layer-specific molding matrices of the respective set have a common generic outer 3D geometrical form. The 3D digital model of the mantle shell 140 may, e.g., define a molding-matrix-specific mantle shell. For example, a set of 3D digital models of mantle shells is provided with a 3D digital model of a mantle shell for each of the 3D digital layer-specific molding matrices of the set of 3D digital layer-specific molding matrices. Each of the 3D digital models of the mantle shells is a negative of an outer 3D geometrical form of the 3D digital layer-specific molding matrix, to which the respective 3D digital model of a mantle shell is assigned. For example, each of the 3D digital layer-specific molding matrices of the set of 3D digital layer-specific molding matrices may have an individual outer 3D geometrical form.

The mantle shell defined by the 3D digital model of a mantle shell 140 shown in FIG. 11 is configured to be slipped over a layer-specific molding matrix, e.g., a layer-specific molding matrix defined by the 3D digital layer-specific molding matrix 120. The mantle shell may provide structural support to the layer-specific molding matrix. The mantle shell may, e.g., be manufactured from a material more rigid than a material, from which the layer-specific molding matrix is manufactured. The inner surfaces of the 3D digital model of the mantle shell 140 configured to be in contact with the outer surfaces of the 3D digital layer-specific molding matrix 120 may have a simpler 3D geometry than the inner surfaces of the 3D digital layer-specific molding matrix 120 configured for providing the 3D geometry of the layer to be reconstructed on the teeth of the patient. The simpler 3D geometry, e.g., with straight faces, may facilitate a removal of the mantle shell defined by the 3D digital model of the mantle shell 140 from the layer-specific molding matrix defined by the 3D digital layer-specific molding matrix 120, despite of its more rigid material. The more flexible material of the layer-specific molding matrix may facilitate a removal of the layer-specific molding matrix, e.g., defined by the 3D digital layer-specific molding matrix 120, from the teeth in the patient's oral cavity, despite of its more complex geometry. Furthermore, a sectional plane 142 extending perpendicularly through the 3D digital model of the mantle shell 140 and the 3D digital layer-specific molding matrix 120 is indicated is indicted in FIG. 11.

FIG. 12 shows a cross-sectional view of a sectional plane 142 of FIG. 11 through the 3D digital model of the mantle shell 140 and the 3D digital layer-specific molding matrix 120. The 3D digital model of the mantle shell 140 provides a reception for receiving the layer-specific molding matrix 120 defined by the 3D digital layer-specific molding matrix 120. The reception of the mantle shell may comprise straight internal side-faces. The layer-specific molding matrix may comprise straight external side-faces in contact with the straight internal side-faces of the mantle shell, when the mantle shell is slipped over the layer-specific molding matrix.

For example, the reception of the 3D digital model of the mantle shell 140 may have a U-shaped cross section as depicted in FIG. 12. The outer 3D geometrical form of the 3D digital layer-specific molding matrix 120 may comprise a matching U-shaped cross section.

For example, the mantle shell defined by the 3D digital model of the mantle shell 140 is manufactured using a material which is more rigid than a material used for manufacturing the layer-specific molding matrix defined by the 3D digital layer-specific molding matrix 120. Thus, the mantle shell may provide stability to the layer-specific molding matrix, while the layer-specific molding matrix due to its higher flexibility is easier removable from the teeth in the patient's oral cavity.

FIG. 13 shows a cross-sectional view of a sectional plane 142 through the 3D digital model of the mantle shell 140 without a 3D digital layer-specific molding matrix 120. The 3D digital model of the mantle shell 140 may comprise a reception 144, e.g., with a U-shaped cross section, configured for receiving the digital layer-specific molding matrix as defined by a 3D digital layer-specific molding matrix 120.

FIG. 14 shows a 3D digital model of the mantle shell 140 with injection channels 146 and venting channels 148. The injection channels 146 are configured for injecting layer-specific reconstruction material into the recesses of a layer-specific molding matrix defined by a 3D digital layer-specific molding matrix, over which the mantle shell defined by the 3D digital model of the mantle shell 140 may be slipped. The 3D digital layer-specific molding matrix defining the respective layer-specific molding matrix may, e.g., be the 3D digital layer-specific molding matrix 100 of FIG. 1, the 3D digital layer-specific molding matrix 110 of FIG. 2, or the 3D digital layer-specific molding matrix 120 of FIG. 3. The injection channels 146 of the 3D digital model of the mantle shell 140 may be aligned with injection channels of the respective 3D digital layer-specific molding matrix. The injection channels 146 of the 3D digital model of the mantle shell 140 may facilitate injecting layer-specific reconstruction material via a mantle shell as defined by the 3D digital model of the mantle shell 140 into a layer-specific molding matrix as defined by the respective 3D digital layer-specific molding matrix.

For injecting the layer-specific reconstruction material via the injection channels 146, an injection device may be used, e.g., a reciprocating pump, like a syringe. The injection channels 146 may each comprise a mouth, e.g., arranged on an occlusal side of the mantle shell defined by the 3D digital model of the mantle shell 140.

The venting channels 148 may be configured for letting out air form the recesses of the layer-specific molding matrix defined by the respective 3D digital layer-specific molding matrix, when layer-specific reconstruction material is injected into the recesses of the layer-specific molding matrix, over which the mantle shell defined by the 3D digital shell mode is slipped. The venting channels 148 of the 3D digital model of the mantle shell 140 may be aligned with the venting channels of the respective 3D digital layer-specific molding matrix. Thus, an effective venting of the layer-specific molding matrix manufactured using the respective 3D digital layer-specific molding matrix as a template may be ensured, when the layer-specific reconstruction material being injected into the layer-specific molding matrix generates an overpressure within the layer-specific molding matrix relative to the environment of the layer-specific molding matrix. The venting channels 148 of the mantle shell defined by the 3D digital model of the mantle shell 140 may be aligned with the venting channels of the layer-specific molding matrix defined by the respective 3D digital layer-specific molding matrix. Mouths of the venting channels 148 may, e.g., be arranged on an occlusal side of the mantle shell defined by the 3D digital model of the mantle shell 140.

FIG. 15 shows an exemplary 3D digital layer-specific molding matrix 160 arranged on a 3D digital teeth model 170. The 3D digital layer-specific molding matrix 160 may be used as a template for manufacturing a layer-specific molding matrix. Such a layer-specific molding matrix may be configured for reconstructing a layer of a tooth 172 to be reconstructed. The 3D digital layer-specific molding matrix 160 comprises a recess 162 configured to receive the tooth 172, on which the layer is to be reconstructed using the layer-specific molding matrix defined by the 3D digital layer-specific molding matrix 160. The recess 162 has a 3D geometric form, which is a negative of the tooth 172 of the patient's oral cavity to be received by the respective recess 162 in combination with the layer to be reconstructed by the respective layer-specific molding matrix. When the 3D digital layer-specific molding matrix 160 is arranged on a 3D digital layer-specific reconstruction model defining a 3D geometric form of a tooth on which the additional layer is to be reconstructed, e.g., the 3D digital teeth model 170 for a first layer on tooth 172, a hollow section remains within the recess 162 defining a 3D geometric form of the additional layer to be reconstructed. When a layer-specific molding matrix manufactured using the 3D digital layer-specific molding matrix 160 is arranged on a tooth in the patient's oral cavity, on which the additional layer is to be reconstructed, a hollow section remains within the recess 162 defining a 3D geometric form of the additional layer to be reconstructed.

Furthermore, the 3D digital layer-specific molding matrix 160 may comprise further recesses 166 for fixating the layer-specific molding matrix defined by the 3D digital layer-specific molding matrix 160 on one or more teeth in the patient's oral cavity. These recesses 166 may have 3D geometric forms, which are negatives of 3D geometric forms of the teeth to be received by the respective recesses 166.

The 3D digital layer-specific molding matrix 160 may further comprise an injection channel configured to insert layer-specific reconstruction material in the recess 162, e.g., by injection. In addition, the 3D digital layer-specific molding matrix 160 may further comprise a venting channel configured for letting out air, when the layer-specific reconstruction material is into the recesses 162 defined by the 3D digital layer-specific molding matrix 160. The injection channel and/or venting channel may, e.g., comprise mouths arranged on an occlusal face of the 3D digital layer-specific molding matrix 160.

The 3D digital layer-specific molding matrix 160 shown in FIG. 15 is one 3D digital layer-specific molding matrix of a set of 3D digital layer-specific molding matrices. The set of 3D digital layer-specific molding matrices may comprise a plurality of 3D digital layer-specific molding matrices, e.g., two, three or four 3D digital layer-specific molding matrices. Each of the 3D digital layer-specific molding matrices defines a layer-specific molding matrix and may be used as a template to manufacture the respective layer-specific molding matrix.

FIG. 16 shows the exemplary 3D digital layer-specific molding matrix 160 of FIG. 15.

FIG. 17 shows an exemplary 3D digital layer-specific molding matrix 161 in form of an exchangeable molding element attachable to a 3D digital holding splint 165. In FIG. 17, the 3D digital layer-specific molding matrix 161 is attached to the 3D digital holding splint 165 and arranged on a 3D digital teeth model 170. In case of the example according to FIG. 17, the same 3D digital holding splint 165 may be used for the reconstruction of each of the layers to be reconstructed. Only the layer-specific molding matrix may be exchanged, such that for each of the layers to be reconstructed the corresponding layer-specific molding matrix is used. The 3D digital layer-specific molding matrix 161 may comprise holding extensions 163 configured to establish a non-destructively detachable connection with the 3D digital holding splint 165. For example, the non-destructively detachable connection may be a snap fit. For example, the 3D digital layer-specific molding matrix 161 may comprise a lateral holding extension 163 on each approximal side of the 3D digital layer-specific molding matrix 161. The lateral holding extension 163 may be extensions of an occlusal section of the 3D digital layer-specific molding matrix 161. The lateral holding extension 163 may, e.g., be formed like wings. The 3D digital holding splint 165 may, e.g., be formed integrally as one part extending on both approximal sides of the 3D digital layer-specific molding matrix 161. Alternatively, the 3D digital holding splint 165 may, e.g., comprise at least two separate parts, each part being configured to be arranged on one of the two approximal sides of the 3D digital layer-specific molding matrix 161. The two separate parts may be arranged on both sides spaced apart from each other by a cutout.

The 3D digital layer-specific molding matrix 161 may be used as a template for manufacturing an exchangeable layer-specific molding matrix. Furthermore, the 3D digital holding splint may be used as a template for manufacturing a holding splint configured for holding the layer-specific molding matrix. Such an exchangeable layer-specific molding matrix may be configured for reconstructing a layer of a tooth 172 to be reconstructed. The 3D digital layer-specific molding matrix 161 comprises a recess 162 configured to receive the tooth 172, on which the layer is to be reconstructed using the layer-specific molding matrix defined by the 3D digital layer-specific molding matrix 161. The recess 162 has a 3D geometric form, which is a negative of the tooth 172 of the patient's oral cavity to be received by the respective recess 162 in combination with the layer to be reconstructed by the respective layer-specific molding matrix. When the 3D digital layer-specific molding matrix 161 is arranged on a 3D digital layer-specific reconstruction model defining a 3D geometric form of a tooth on which the additional layer is to be reconstructed, e.g., the 3D digital teeth model 170 for a first layer on tooth 172, a hollow section remains within the recess 162 defining a 3D geometric form of the additional layer to be reconstructed. When a layer-specific molding matrix manufactured using the 3D digital layer-specific molding matrix 161 is arranged on a tooth in the patient's oral cavity, on which the additional layer is to be reconstructed, a hollow section remains within the recess 162 defining a 3D geometric form of the additional layer to be reconstructed.

The 3D digital holding splint 165 may comprise further recesses 166 for fixating the holding splint defined by the 3D digital holding splint 165 on one or more teeth in the patient's oral cavity. These recesses 166 may have 3D geometric forms, which are negatives of 3D geometric forms of the teeth to be received by the respective recesses 166.

The exchangeable 3D digital layer-specific molding matrix 161 may further comprise an injection channel configured to insert layer-specific reconstruction material in the recess 162, e.g., by injection. In addition, the exchangeable 3D digital layer-specific molding matrix 161 may further comprise a venting channel configured for letting out air, when the layer-specific reconstruction material is into the recesses 162 defined by the 3D digital layer-specific molding matrix 161. The injection channel and/or venting channel may, e.g., comprise mouths arranged on an occlusal face of the 3D digital layer-specific molding matrix 161.

The exchangeable 3D digital layer-specific molding matrix 161 shown in FIG. 17 is one exchangeable 3D digital layer-specific molding matrix of a set of exchangeable 3D digital layer-specific molding matrices. The set of exchangeable 3D digital layer-specific molding matrices may comprise a plurality of exchangeable 3D digital layer-specific molding matrices, e.g., two, three or four exchangeable 3D digital layer-specific molding matrices. Each of the exchangeable 3D digital layer-specific molding matrices defines a layer-specific molding matrix and may be used as a template to manufacture the respective layer-specific molding matrix. Each of the exchangeable 3D digital layer-specific molding matrices may be configured to be connected to the 3D digital holding splint 165 using one or more non-destructively detachable connections, e.g., snap-fits.

FIG. 18 shows a schematic diagram of an exemplary computer device 10 for providing a set of layer-specific molding matrices for reconstructing layer-by-layer one or more teeth of a set of teeth in a patient's oral cavity. The computer device 10 may be operational with numerous other general-purpose or special-purpose computing system environments or configurations. Computer device 10 may be described in the general context of computer device executable instructions, such as program modules comprising executable program instructions, being executable by the computer device 10. Generally, program modules may include routines, programs, objects, components, logic, data structures, and so on that perform particular tasks or implement particular abstract data types. Computer device 10 may be practiced in distributed computing environments where tasks are performed by remote processing devices that are linked through a communications network. In a distributed computing environment, program modules may be located in both local and remote computer device storage media including memory storage devices.

In FIG. 18, computer device 10 is shown in the form of a general-purpose computing device. The components of computer device 10 may include, but are not limited to, one or more processors or processing units 16, a system memory 28, and a bus 18 that couples various system components including system memory 28 to processor 16. Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus.

Computer device 10 may comprise a variety of computer device readable storage media. Such media may be any available storage media accessible by computer device 10, and include both volatile and non-volatile storage media, removable and non-removable storage media.

A system memory 28 may include computer device readable storage media in the form of volatile memory, such as random-access memory (RAM) 30 and/or cache memory 32. Computer device 10 may further include other removable/non-removable, volatile/non-volatile computer device storage media. For example, storage system 34 may be provided for reading from and writing to a non-removable, non-volatile magnetic media also referred to as a hard drive. For example, a magnetic disk drive for reading from and writing to a removable, non-volatile magnetic disk, e.g., a floppy disk, and an optical disk drive for reading from or writing to a removable, non-volatile optical disk such as a CD-ROM, DVD-ROM or other optical storage media may be provided. In such instances, each storage medium may be connected to bus 18 by one or more data media interfaces. Memory 28 may, e.g., include a 3D digital teeth model of a patient received by the computer device 10. Memory 28 may, e.g., include scan data of a patient's mouth from an intraoral scan or from a scan of a classical mold/impression, e.g., providing information about the surface structure of the patient's intraoral tissue comprising the one or more teeth to be reconstructed. The scan data may comprise scan data of the one or more teeth to be reconstructed.

Memory 28 may, e.g., include a database may be provided comprising data for a plurality of layer-specific reconstruction materials. For each type of layer of a plurality of different types of layers, one or more reconstruction materials may be identified as layer-specific reconstruction materials. For each of the layer-specific reconstruction material a minimum thickness required by the layer-specific reconstruction material in order to ensure a sufficient structural strength may be defined. Furthermore, different color and/or degrees of transparency may be defined in the database and assigned to each of the layer-specific reconstruction materials. Memory 28 may, e.g., include a tooth library providing a plurality of artificial teeth. Memory 28 may, e.g., comprise one or more trained or machine learning modules to be trained. The trained machine learning modules may, e.g., be configured to provide the 3D digital layer-specific molding matrices as output in response to receiving the 3D digital teeth model as input. The trained machine learning modules may, e.g., be configured to provide the 3D digital layer-specific reconstruction models as output in response to receiving the 3D digital teeth model as input. The one or more trained machine learning modules may, e.g., have been received by the computer device 10. The one or more trained machine learning modules may, e.g., have been trained by the computer device 10 using training datasets with training data received and/or generated by the computer device 10. For training one or more machine learning module, the memory 28 may comprise one or more machine learning modules to be trained as well as the training datasets with training data. The one or more machine learning modules to be trained may, e.g., be untrained machine learning modules, pre-trained machine learning modules or partially trained machine learning modules.

Program 40 may have a set of one or more program modules 42 and by way of example be stored in memory 28. The program modules 42 may comprise an operating system, one or more application programs, other program modules, and/or program data. Each of the operating system, one or more application programs, other program modules, and program data or some combination thereof, may include an implementation of a networking environment. One or more of the program modules 42 may be configured for providing an ordered set of layer-specific molding matrices for reconstructing layer-by-layer one or more teeth of a set of teeth in a patient's oral cavity. The program modules 42 may, e.g., further be configured for generating an ordered set of layer-specific reconstruction models. Each of the 3D digital layer-specific reconstruction models according to the order may add another layer to be reconstructed to the 3D digital teeth model. One of the program modules 42 may, e.g., be configured to suggest thicknesses of reconstruction layers for reconstructing teeth. One of the program modules 42 may, e.g., be configured to use one or more of the trained machine learning modules for providing the 3D digital layer-specific molding matrices or for providing the 3D digital layer-specific reconstruction models. One of the program modules 42 may, e.g., be configured to train one or more of the aforementioned machine learning modules to be trained to provide the 3D digital layer-specific molding matrices or to provide the 3D digital layer-specific reconstruction models. The machine learning modules to be trained may, e.g., be untrained machine learning modules, pre-trained machine learning modules or partially trained machine learning modules. Computer device 10 may further communicate with one or more external devices 14 such as a keyboard, a pointing device, like a mouse, and a display 24 enabling a user to interact with computer device 10. Such communication can occur via input/output (I/O) interfaces 22. Computer device 10 may further communicate with one or more networks such as a local area network (LAN), a general wide area network (WAN), and/or a public network, like the Internet, via network adapter 20. Network adapter 20 may communicate with other components of computer device 10 via bus 18. It should be understood that although not shown, other hardware and/or software components could be used in conjunction with computer device 10.

The computer device 10 shown in FIG. 18 may be configured for providing a set of layer-specific molding matrices for reconstructing layer-by-layer one or more teeth of a set of teeth in a patient's oral cavity. The computer device 10 may be a standalone computer with no network connectivity that may receive data to be processed through a local interface. The data received by computer device 10 may for example comprise scan data of a patient's mouth from an intraoral scan or from a scan of a classical mold/impression, e.g., providing information about the surface structure of the patient's intraoral tissue comprising the one or more teeth to be reconstructed. This data may be used to provide a 3D digital teeth model of the set of teeth in the patient's oral cavity comprising the one or more teeth to be reconstructed. Alternatively, the data received may, e.g., comprise the 3D digital teeth model. The 3D digital teeth model may, e.g., be used to generated a set of 3D digital layer-specific reconstruction models. Alternatively, the data received may, e.g., comprise the set of 3D digital layer-specific reconstruction models. The set of 3D digital layer-specific reconstruction models may be an ordered set. Each of the 3D digital layer-specific reconstruction models according to the order may add another one of the layers to be reconstructed to the 3D digital teeth model. The set of 3D digital layer-specific reconstruction models may be used to generate the set of 3D digital layer-specific molding matrices. Each of the 3D digital layer-specific molding matrices may be a negative of one of the 3D digital layer-specific reconstruction models. The data received by computer device 10 may, e.g., comprise a tooth library providing a plurality of artificial teeth.

The data received by computer device 10 may for example comprise one or more machine learning modules to be trained. The machine learning modules to be trained may, e.g., be untrained machine learning modules, pre-trained machine learning modules or partially trained machine learning modules. The data received by computer device 10 may for example comprise training datasets, e.g., for training the one or more machine learning modules to be trained for providing the 3D digital layer-specific molding matrices as output in response to receiving the 3D digital teeth model as input. The one or more machine learning modules to be trained may, e.g., be trained for providing the 3D digital layer-specific reconstruction models as output in response to receiving the 3D digital teeth model as input. The data received by computer device 10 may for example comprise one or more trained machine learning modules trained to provide the 3D digital layer-specific molding matrices as output in response to receiving the 3D digital teeth model as input. The trained machine learning modules may, e.g., be trained to provide the 3D digital layer-specific reconstruction models as output in response to receiving the 3D digital teeth model as input.

The computer device 10 may be used to provide the templates for manufacturing the set of layer-specific molding matrices, i.e., the ordered set of 3D digital layer-specific molding matrices. Such operation may, however, likewise be performed using a computer device that is connected to a network such as a communications network and/or a computing network.

FIG. 19 shows an exemplary computer device 10 for providing a set of layer-specific molding matrices for reconstructing layer-by-layer one or more teeth of a set of teeth in a patient's oral cavity. The computer device 10 may, e.g., be configured as shown in FIG. 18. The computer device 10 may comprise a hardware component 54 comprising one or more processors as well as a memory storing machine-executable program instructions. Execution of the program instructions by the one or more processors may cause the one or more processors to control the computer device 10 to provide the set of layer-specific molding matrices for reconstructing layer-by-layer one or more teeth of a set of teeth in a patient's oral cavity.

The set of layer-specific molding matrices may comprise two or more layer-specific molding matrices. Each of the layer-specific molding matrices may be configured for being arranged on the set of teeth and for casting a different layer of the one or more teeth to be reconstructed with a layer-specific reconstruction material inserted into the respective layer-specific molding matrix. The respective layer-specific molding matrix may define a 3D geometric form of the respective layer being casted. A 3D digital teeth model of the set of teeth in the patient's oral cavity may be provided comprising the one or more teeth to be reconstructed. Using the 3D digital teeth model, e.g., an ordered set of 3D digital layer-specific reconstruction models may be generated. Each of the 3D digital layer-specific reconstruction models according to the order may add another one of the layers to be reconstructed to the 3D digital teeth model. Using the ordered set of 3D digital layer-specific reconstruction models an ordered set of 3D digital layer-specific molding matrices may be generated. Each of the 3D digital layer-specific molding matrices may be a negative of one of the 3D digital layer-specific reconstruction models. The ordered set of 3D digital layer-specific molding matrices may be provided as a set of templates for manufacturing the set of layer-specific molding matrices.

The computer device 10 may further comprise one or more input devices, like a keyboard 58 and a mouse 56, enabling a user to interact with the computer device 10. Furthermore, the computer device 10 may comprise one or more output devices, like a display 24 providing a graphical user interface 50 with control elements 52, e.g., GUI elements, enabling the user to control the providing of a set of layer-specific molding matrices for reconstructing layer-by-layer one or more teeth of a set of teeth in a patient's oral cavity. The set of layer-specific molding matrices is defined by a set of 3D digital layer-specific molding matrices, e.g., comprising the layer-specific molding matrices 100, 110. Furthermore, the control elements 52 may, e.g., be used to generate, adjust and/or modify a 3D digital teeth model of a set of teeth in the patient's oral cavity, a set of 3D digital layer-specific reconstruction models and/or one or more 3D digital models of a mantle shells.

Furthermore, the computer device 10 may for example comprise a scanner 59, e.g., an optical scanner, for acquiring scan data of a patient's intraoral tissue. The scan data may, e.g., be direct scan data of a patient's mouth from an intraoral scan or indirect scan data from a scan of a classical mold/impression, e.g., providing information about the surface structure of the patient's intraoral tissue comprising the one or more teeth to be reconstructed. This data may be used to provide a 3D digital teeth model of the set of teeth in the patient's oral cavity comprising the one or more teeth to be reconstructed.

FIG. 20 shows an exemplary manufacturing system 11 for manufacturing a set of physical layer-specific molding matrices using a set of 3D digital layer-specific molding matrices as a set of templates comprising, e.g., the layer-specific molding matrix 100 as shown in FIG. 1 as well as the layer-specific molding matrix 110 as shown in FIG. 2. The physical layer-specific molding matrices of the set of physical layer-specific molding matrices are physical copy of the respective templates. For example, the physical layer-specific molding matrix 101 is a physical copy of the layer-specific molding matrix 100. For example, the physical layer-specific molding matrix 111 is a physical copy of the layer-specific molding matrix 110. The physical layer-specific molding matrices may be used to reconstruct layer-by-layer one or more teeth of a set of teeth in a patient's oral cavity. Furthermore, the manufacturing system 11 may be configured for manufacturing one or more physical mantle shells using one or more 3D digital models of mantle shells as templates. The manufactured one or more mantle shells are physical copies of the respective template.

The manufacturing system 11 may comprise the computer device 10 of FIG. 19. The computer device 10 may further be configured to control one or more manufacturing devices 60, 70. For example, the manufacturing system 11 may comprise a manufacturing device in form of a machining device 70 controlled by the computer device 10. The machining device 70 may be configured to machining a blank 76 using one or more machining tools 72. The blank 76 of raw material 78 may be provided using a holding device 74 and cut into a desired shape and size of the one or more elements to be manufactured, e.g., one or more physical layer-specific molding matrices of a set of layer-specific molding matrices as defined by a set of 3D digital layer-specific molding matrices, using the one or more machining tools 72 for executing a controlled material-removal process. The manufactured physical layer-specific molding matrix may, e.g., be a physical layer-specific molding matrix 101 as defined by the 3D digital layer-specific molding matrix 100. The machining tool 72 may, e.g., be a milling tool. A 3D digital model, e.g., the 3D digital layer-specific molding matrix 100, may provide a template for the element being manufactured using the machining device 70, e.g., the physical layer-specific molding matrix 101.

For example, the machining device 70 may further be used to manufacture one or more mantle shells using, e.g., one or more 3D digital models of mantle shells as templates.

For example, the manufacturing system 11 may comprise a manufacturing device in form of a 3D printing device 60. The 3D printing device 60 may be controlled by the computer device and configured to print one or more elements to be manufactured, e.g., one or more physical layer-specific molding matrices of a set of layer-specific molding matrices as defined by a set of 3D digital layer-specific molding matrices. The manufactured physical layer-specific molding matrix may, e.g., be a physical layer-specific molding matrix 111 as defined by the 3D digital layer-specific molding matrix 110. The 3D printing device 60 may comprise a printing element 62 configured to print the respective element, like the layer-specific molding matrix 111, layer by layer. The printing element 62 may, e.g., comprise a nozzle configured for distributing printing material. A 3D digital model, e.g., the 3D digital layer-specific molding matrix 110, may provide a template of the physical element manufactured using the 3D printing device 60, e.g., the physical layer-specific molding matrix 111.

For example, the 3D printing device 60 may further be used to manufacture one or more mantle shells using, e.g., one or more 3D digital models of mantle shells as templates.

FIG. 21 shows an exemplary method for providing templates for an ordered set of layer-specific molding matrices. The templates are provided in form of an ordered set of 3D digital layer-specific molding matrices. In block 300, a 3D digital teeth model of a set of teeth in the patient's oral cavity is provided. The set of teeth comprises one or more teeth to be reconstructed. The 3D digital teeth model may, e.g., be in form of a tissue model comprising in addition to the hard tissue, i.e., the set of teeth, soft tissue, like the gingiva. The 3D digital teeth model provides an initial setup for defining are layer-by-layer reconstruction of one or more of the patient's teeth in the patient's oral cavity. The layer-by-layer reconstruction is defined by an ordered set of 3D digital layer-specific reconstruction models. The ordered set of 3D digital layer-specific reconstruction models comprises a plurality of 3D digital layer-specific reconstruction models, e.g., two, three, or four models. According to the order, a first one of the 3D digital layer-specific reconstruction models adds a first layer to be reconstructed to the teeth of the 3D digital teeth model to be reconstructed. A second one of the 3D digital layer-specific reconstruction models adds a second layer to be reconstructed to the teeth of the first one of the first 3D digital layer-specific reconstruction models and so on. In case of a third or fourth 3D digital layer-specific reconstruction model, third or fourth 3D digital layer-specific reconstruction model adds a third or fourth layer to be reconstructed to the teeth of the second or third 3D digital teeth model, respectively. Thus, each of the 3D digital layer-specific reconstruction models according to the order adds another one of the layers to be reconstructed to the 3D digital teeth model. The first 3D digital layer-specific reconstruction model corresponds to the 3D digital teeth model plus one layer added, the second 3D digital layer-specific reconstruction model corresponds to the 3D digital teeth model plus two layers added, the third 3D digital layer-specific reconstruction model corresponds to the 3D digital teeth model plus three layers added and so on. In other words, the n-th 3D digital layer-specific reconstruction model according to the order of the set corresponds to the 3D digital teeth model plus n layers added with n being a natural number, i.e., a positive integer.

The 3D digital teeth model may be received via a network, read from a storage medium or generated using scan data of the tissue. The scan data may, e.g., be scanned data acquired using an optical scanner. The scan data may be scanned data resulting from an intraoral scan, from a scan of an impression of the natural tissue, in particular the teeth, or from a scan from of a physical tissue model generated using the impression of the natural tissue, in particular the teeth.

In block 302, e.g., the ordered set of 3D digital layer-specific reconstruction models is generated using the 3D digital teeth model as an initial setup. The ordered set of 3D digital layer-specific reconstruction models defines a layer-by-layer reconstruction of one or more of the patient's teeth in the patient's oral cavity starting with the 3D digital teeth model. The n-th 3D digital layer-specific reconstruction model according to the order of the set corresponds to the 3D digital teeth model plus n layers added with n being a natural number, i.e., a positive integer.

In block 304, the ordered set of 3D digital layer-specific reconstruction models is used to generate an ordered set of 3D digital layer-specific molding matrices. Each of the 3D digital layer-specific molding matrices is a negative of one of the 3D digital layer-specific reconstruction models. Thus, for each of the 3D digital layer-specific reconstruction models of the set of 3D digital layer-specific reconstruction models an associated 3D digital layer-specific molding matrix is provided. The 3D digital layer-specific molding matrix is a negative of one of the 3D digital layer-specific reconstruction model. Thus, arranging the n-th 3D digital layer-specific molding matrix, which is a negative of the n-th 3D digital layer-specific reconstruction model, on the (n−1)-th 3D digital layer-specific reconstruction model, a hollow space is defined between outer surface sections of the teeth (n−1)-th 3D digital layer-specific reconstruction model to be reconstructed and the inner surface sections of recesses of the n-th 3D digital layer-specific molding matrix. The hollow space defines the 3D geometric form of the n-th layer to be added to the (n−1)-th 3D digital layer-specific reconstruction model using the n-th 3D digital layer-specific reconstruction model. Adding the n-th layer to be added to the (n−1)-th 3D digital layer-specific reconstruction model results in the n-th 3D digital layer-specific reconstruction model. The (n−1)-th 3D digital layer-specific reconstruction model in case of the n=1 is the 3D digital teeth model. Thus, using layer-specific molding matrices as defined by the 3D digital layer-specific molding matrices one or more teeth in a patient's oral cavity may be reconstruct layer-by-layer starting with an initial setup as resembled by the 3D digital teeth model. The layer-specific molding matrices may be used according to the order defined for the layer-specific molding matrices of the set of layer-specific molding matrices resembling the order of the ordered set of 3D digital layer-specific molding matrices.

In block 306, the ordered set of 3D digital layer-specific molding matrices is provided as a set of templates for manufacturing the set of layer-specific molding matrices. In block 308, the layer-specific molding matrices forming the set of layer-specific molding matrices is manufactured using the ordered set of 3D digital layer-specific molding matrices.

Each of the manufactured layer-specific molding matrices of the set of layer-specific molding matrices is a physical copy of one of the templates. The layer-specific molding matrices may, e.g., be manufactured using machining, 3D printing or casting. The order of the ordered set of 3D digital layer-specific molding matrices refers to the order of usage of the layer-specific molding matrices in order to reconstruct the teeth layer-by-layer. The manufacturing of the layer-specific molding matrices may be executed independently of this order. Multiple or all of the layer-specific molding matrices may, e.g., be manufactured in parallel and/or sequentially. In case of a sequential manufacturing, the sequence may be independent of the respective order.

In order to use the manufactured set of the layer-specific molding matrices for reconstructing layer-by-layer the one or more teeth in the patient's oral cavity, the layer-specific molding matrices are arranged one after another following the order defined for the layer-by-layer-reconstruction on the teeth in the patient's oral cavity. In each of the layer-specific molding matrices arranged on the teeth in the patient's oral cavity, a layer-specific reconstruction material is inserted into the respective layer-specific molding matrix. The layer-specific reconstruction material is inserted into the remaining free space of one or more recesses of the respective layer-specific molding matrix arranged on the teeth. The remaining free space defines a 3D geometrical form of the layer to be reconstructed using the respective layer-specific molding matrix and the layer-specific reconstruction material. For example, the layer-specific reconstruction material is injected via one or more injecting channels of the respective layer-specific molding matrix. After the inserted layer-specific reconstruction material is cured, the respective layer-specific molding matrix may be removed. The reconstructed layer may, if necessary, be finalized, e.g., final adjustments may be performed. Then the reconstruction may be continued using the next layer-specific molding matrix of the set of layer-specific molding matrices according to the order of the layer-by-layer-reconstruction.

FIG. 22 shows an exemplary method for manufacturing one or more mantle shells. In block 310, a set of 3D digital layer-specific molding matrices is provided. In block 312, one or more 3D digital models of mantle shells are generated. For example, a 3D digital model of a single generic mantle shell is generated, which is configured to be slipped over each of the layer-specific molding matrices as defined by the 3D digital layer-specific molding matrices, when the respective layer-specific molding matrix is arranged on the patient. Thus, the generic mantle shell may be configured to provide structural support to each of the layer-specific molding matrices as defined by the 3D digital layer-specific molding matrices. For example, all the 3D digital layer-specific molding matrices may comprise an identical generic outer 3D geometrical form. With the 3D digital model of the mantle shell being configured as a negative of this generic outer 3D geometrical form, it may fit over each of the layer-specific molding matrices as defined by the 3D digital layer-specific molding matrices.

Alternatively, a plurality of 3D digital models of mantle shells may be provided. For example, an individual 3D digital model of a mantle shell may be provided for each layer-specific molding matrices as defined by the 3D digital layer-specific molding matrices. Each of the 3D digital models of a mantle shell may be a negative of an outer 3D geometrical form of the 3D digital layer-specific molding matrix for which the mantle shell is provided. Different 3D digital layer-specific molding matrices may have different outer 3D geometrical forms. The individual 3D digital model of the individual mantle shells may be adjusted to the individual outer 3D geometrical forms of the individual 3D digital layer-specific molding matrices. The respective 3D digital model of the mantle shell is configured to be slipped over a layer-specific molding matrix defined by the respective 3D digital layer-specific molding matrix arranged on the patient's teeth in the patient's oral cavity. The individual mantle shell provides structural support to the layer-specific molding matrix defined by the respective 3D digital layer-specific molding matrix.

In block 314, the one or more 3D digital models of the mantle shells are provided as templates for manufacturing one or more physical copies of the one or more 3D digital models of the mantle shells. In block 316, one or more physical mantle shells are manufactured using the one or more 3D digital models. Each of the one or more manufactured physical mantle shells is a physical copy of one of the templates. The mantle shells may, e.g., be manufactured using machining, 3D printing or casting. The one or more mantle shell may, e.g., be manufactured from a material more rigid than a material, from which the layer-specific molding matrices of the set of layer-specific molding matrices are manufactured. The inner surfaces of the mantle shell in contact with the outer surfaces of one of the layer-specific molding matrices of the set of layer-specific molding matrices may have a simpler 3D geometry than the inner surfaces of the respective layer-specific molding matrix in contact with surfaces of the natural tissue in the patient's oral cavity. The simpler 3D geometry, e.g., with straight faces, may facilitate a removal of the mantle shell from the layer-specific molding matrix, despite of its more rigid material. The more flexible material of the layer-specific molding matrix may facilitate a removal of the layer-specific molding matrix from the natural tissue teeth in the patient's oral cavity, in particular the teeth, despite of its more complex geometry.

FIG. 23 shows an exemplary method for providing a trained machine learning module trained to provide an ordered set 3D digital layer-specific reconstruction models as output in response to receiving a 3D digital teeth model as input. In block 320, a machine learning module to be trained is provided. The machine learning module to be trained may, e.g., be an untrained machine learning module, a pre-trained machine learning module or a partially trained machine learning module. In block 322, a set of training datasets is provided for training the machine learning module to be trained. Each training dataset may comprise a 3D digital training teeth model and an ordered set of 3D digital layer-specific training reconstruction models. In addition, further training data may, e.g., be provided as input by the training datasets. For example, the training input data provided by the training datasets may further comprise one or more of the following in addition to the 3D digital training teeth model: a target color of the one or more teeth to be reconstructed, e.g., defined by the color of a neighboring tooth or by a selected color from set of predefined colors, target degrees of transparency of the reconstructed layers of the one or more teeth to be reconstructed, e.g., defined by the degree of transparency of layers of a neighboring tooth, a target form of the one or more teeth to be reconstructed, one or more minimum thicknesses required by the layer-specific reconstruction materials intended to be used for casting one or more respective layers, a number of layers to be reconstructed, definition of types of layers to be reconstructed.

In block 324, the machine learning module to be trained provided in block 320 is trained using the set of training datasets provided in block 322. The machine learning module to be trained is trained to provide the 3D digital layer-specific training reconstruction models of the ordered set of 3D digital layer-specific training reconstruction models of the training datasets as output in response to receiving the 3D digital training teeth models of the respective training datasets as input. In block 326, the trained machine learning module resulting from block 324 is provide. The provided trained machine learning module may be used to provide 3D digital layer-specific reconstruction models as output in response to receiving a 3D digital teeth model as input.

FIG. 24 shows an exemplary method for using a trained machine learning module for generating the 3D digital layer-specific reconstruction models of the ordered set of 3D digital layer-specific reconstruction models. In block 330, the trained machine learning module is provided. The providing may comprise a training of a machine learning module to be trained as shown in FIG. 23. The trained machine learning module may be configured to provide 3D digital layer-specific reconstruction models as output in response to receiving a 3D digital teeth model as input. In block 332, the 3D digital teeth model is input into the trained machine learning module. Thus, the trained machine learning module receives the 3D digital teeth model as input. In addition, further data may, e.g., be provided as input to the trained machine learning module depending on the training of the machine learning module. For example, the input provided to the machine learning module may further comprise one or more of the following: a target color of the one or more teeth to be reconstructed, e.g., defined by the color of a neighboring tooth or by a selected color from set of predefined colors, target degrees of transparency of the reconstructed layers of the one or more teeth to be reconstructed, e.g., defined by the degree of transparency of layers of a neighboring tooth, a target form of the one or more teeth to be reconstructed, one or more minimum thicknesses required by the layer-specific reconstruction materials intended to be used for casting one or more respective layers, a number of layers to be reconstructed, definition of types of layers to be reconstructed.

In block 334, the 3D digital layer-specific reconstruction models are received from the trained machine learning module as output in response to the inputting of the 3D digital teeth model. Thus, the trained machine learning module outputs the 3D digital layer-specific reconstruction models in response to the receiving of the 3D digital teeth model. In block 336, the output 3D digital layer-specific reconstruction models are provided, e.g., for generating the ordered set of 3D digital layer-specific reconstruction matrices.

FIG. 25 shows an exemplary method for providing a trained machine learning module trained to provide an ordered set 3D digital layer-specific molding matrices as output in response to receiving a 3D digital teeth model as input. In block 340, the machine learning module to be trained is provided. The machine learning module to be trained may, e.g., be an untrained machine learning module, a pre-trained machine learning module or a partially trained machine learning module. In block 342, a set of training datasets is provided for training the machine learning module to be trained. Each training dataset may comprise a 3D digital training teeth model and an ordered set of 3D digital layer-specific training molding matrices. In addition, further training data may, e.g., be provided as input by the training datasets. For example, the training input data provided by the training datasets may further comprise one or more of the following in addition to the 3D digital training teeth model: a target color of the one or more teeth to be reconstructed, e.g., defined by the color of a neighboring tooth or by a selected color from set of predefined colors, target degrees of transparency of the reconstructed layers of the one or more teeth to be reconstructed, e.g., defined by the degree of transparency of layers of a neighboring tooth, a target form of the one or more teeth to be reconstructed, one or more minimum thicknesses required by the layer-specific reconstruction materials intended to be used for casting one or more respective layers, a number of layers to be reconstructed, definition of types of layers to be reconstructed.

In block 344, the machine learning module to be trained provided in block 340 is trained using the set of training datasets provided in block 342. The machine learning module to be trained is trained to provide the 3D digital layer-specific training molding matrices of the ordered set of 3D digital layer-specific training molding matrices of the training datasets as output in response to receiving the 3D digital training teeth models of the respective training datasets as input. In block 346, the trained machine learning module resulting from block 344 is provide. The provided trained machine learning module may be used to provide 3D digital layer-specific molding matrices as output in response to receiving a 3D digital teeth model as input.

FIG. 26 shows an exemplary method for using a trained machine learning module for generating the 3D digital layer-specific molding matrices of the ordered set of 3D digital layer-specific molding matrices. In block 350, the trained machine learning module is provided. The providing may comprise a training of a machine learning module to be trained as shown in FIG. 25. The trained machine learning module may be configured to provide 3D digital layer-specific molding matrices as output in response to receiving a 3D digital teeth model as input. In block 352, the 3D digital teeth model is input into the trained machine learning module. Thus, the trained machine learning module receives the 3D digital teeth model as input. In addition, further data may, e.g., be provided as input to the trained machine learning module depending on the training of the machine learning module. For example, the input provided to the machine learning module may further comprise one or more of the following: a target color of the one or more teeth to be reconstructed, e.g., defined by the color of a neighboring tooth or by a selected color from set of predefined colors, target degrees of transparency of the reconstructed layers of the one or more teeth to be reconstructed, e.g., defined by the degree of transparency of layers of a neighboring tooth, a target form of the one or more teeth to be reconstructed, one or more minimum thicknesses required by the layer-specific reconstruction materials intended to be used for casting one or more respective layers, a number of layers to be reconstructed, definition of types of layers to be reconstructed.

In block 354, the 3D digital layer-specific molding matrices are received from the trained machine learning module as output in response to the inputting of the 3D digital teeth model. Thus, the trained machine learning module outputs the 3D digital layer-specific molding matrices in response to the receiving of the 3D digital teeth model. In block 356, the output 3D digital layer-specific molding matrices are provided, e.g., for manufacturing a set of layer-specific molding matrices using the 3D digital layer-specific molding matrices of the ordered set of 3D digital layer-specific reconstruction matrices as templates.

While the invention has been illustrated and described in detail in the drawings and foregoing description, such illustration and description are to be considered illustrative or exemplary and not restrictive; the invention is not limited to the disclosed embodiments.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measured cannot be used to advantage. Any reference signs in the claims should not be construed as limiting the scope.

A single processor or other unit may fulfill the functions of several items recited in the claims. A computer program may be stored/distributed on a suitable medium, such as an optical storage medium or a solid-state medium supplied together with or as part of other hardware, but may also be distributed in other forms, such as via the Internet or other wired or wireless telecommunication systems.

As will be appreciated by one skilled in the art, aspects of the present invention may be embodied as an apparatus, method, computer program or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer executable code embodied thereon. A computer program comprises the computer executable code or "program instructions".

Any combination of one or more computer readable medium(s) may be utilized. The computer readable medium may be a computer readable signal medium or a computer readable storage medium. A "computer-readable storage medium" as used herein encompasses any tangible storage medium which may store instructions which are executable by a processor of a computing device. The computer-readable storage medium may be referred to as a computer-readable non-transitory storage medium. The computer-readable storage medium may also be referred to as a tangible computer readable medium. In some embodiments, a computer-readable storage medium may also be able to store data which is able to be accessed by the processor of the computing device. Examples of computer-readable storage media include, but are not limited to: a floppy disk, a magnetic hard disk drive, a solid-state hard disk, flash memory, a USB thumb drive, Random Access Memory (RAM), Read Only Memory (ROM), an optical disk, a magneto-optical disk, and the register file of the processor. Examples of optical disks include Compact Disks (CD) and Digital Versatile Disks (DVD), for example CD-ROM, CD-RW, CD-R, DVD-ROM, DVD-RW, or DVD-R disks. A further example of an optical disk may be a Blu-ray disk. The term computer readable-storage medium also refers to various types of recording media capable of being accessed by the computer device via a network or communication link. For example, a data may be retrieved over a modem, over the internet, or over a local area network. Computer executable code embodied on a computer readable medium may be transmitted using any appropriate medium, including but not limited to wireless, wireline, optical fiber cable, RF, etc., or any suitable combination of the foregoing.

A computer readable signal medium may include a propagated data signal with computer executable code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

"Computer memory" or "memory" is an example of a computer-readable storage medium. Computer memory is any memory which is directly accessible to a processor. "Computer storage" or "storage" is a further example of a computer-readable storage medium. Computer storage is any non-volatile computer-readable storage medium. In some embodiments, computer storage may also be computer memory or vice versa.

A "processor" as used herein encompasses an electronic component which is able to execute a program or machine executable instruction or computer executable code. References to the computing device comprising "a processor" should be interpreted as possibly containing more than one processor or processing core. The processor may for instance be a multi-core processor. A processor may also refer to a collection of processors within a single computer device or distributed amongst multiple computer devices. The term computing device should also be interpreted to possibly refer to a collection or network of computing devices each comprising a processor or processors. The computer executable code may be executed by multiple processors that may be within the same computing device or which may even be distributed across multiple computing devices.

Computer executable code may comprise machine executable instructions or a program which causes a processor to perform an aspect of the present invention. Computer executable code for carrying out operations for aspects of the present invention may be written in any combination of one or more programming languages, including an object-oriented programming language such as Java, Smalltalk, C++ or the like and conventional procedural programming languages, such as the "C" programming language or similar programming languages and compiled into machine executable instructions. In some instances, the computer executable code may be in the form of a high-level language or in a pre-compiled form and be used in conjunction with an interpreter which generates the machine executable instructions on the fly.

The computer executable code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Generally, the program instructions can be executed on one processor or on several processors. In the case of multiple processors, they can be distributed over several different entities like clients, servers etc. Each processor could execute a portion of the instructions intended for that entity. Thus, when referring to a system or process involving multiple entities, the computer program or program instructions are understood to be adapted to be executed by a processor associated or related to the respective entity.

A "user interface" as used herein is an interface which allows a user or operator to interact with a computer or computer device. A 'user interface' may also be referred to as a 'human interface device.' A user interface may provide information or data to the operator and/or receive information or data from the operator. A user interface may enable input from an operator to be received by the computer and may provide output to the user from the computer. In other words, the user interface may allow an operator to control or manipulate a computer and the interface may allow the computer indicate the effects of the operator's control or manipulation. The display of data or information on a display or a graphical user interface is an example of providing information to an operator. The receiving of data through a keyboard, mouse, trackball, touchpad, pointing stick, graphics tablet, joystick, gamepad, webcam, headset, gear sticks, steering wheel, pedals, wired glove, dance pad, remote control, one or more switches, one or more buttons, and accelerometer are all examples of user interface components which enable the receiving of information or data from an operator.

A GUI element is a data object some of which's attributes specify the shape, layout and/or behavior of an area displayed on a graphical user interface, e.g., a screen. A GUI element can be a standard GUI element such as a button, a text box, a tab, an icon, a text field, a pane, a check-box item or item group or the like. A GUI element can likewise be an image, an alphanumeric character or any combination thereof. At least some of the properties of the displayed GUI elements depend on the data value aggregated on the group of data object said GUI element represents.

Aspects of the present invention are described with reference to flowchart illustrations and/or block diagrams of methods, apparatus (systems) and computer program products according to embodiments of the invention. It will be understood that each block or a portion of the blocks of the flowchart, illustrations, and/or block diagrams, can be implemented by computer program instructions in form of computer executable code when applicable. It is further understood that, when not mutually exclusive, combinations of blocks in different flowcharts, illustrations, and/or block diagrams may be combined. These computer program instructions may be provided to a processor of a general-purpose computer, special-purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer-implemented process such that the instructions which execute on the computer or other programmable apparatus provide processes for implementing the functions/acts specified in the flowchart and/or block diagram block or blocks.

Possible advantageous embodiments may comprise the following combinations of features:
1. A computer-implemented method for providing a set of layer-specific molding matrices for reconstructing layer-by-layer one or more teeth of a set of teeth in a patient's oral cavity, the set of layer-specific molding matrices comprising two or more layer-specific molding matrices, each of the layer-specific molding matrices being configured for being arranged on the set of teeth and for casting a different layer of the one or more teeth to be reconstructed with a layer-specific reconstruction material inserted into the respective layer-specific molding matrix with the respective layer-specific molding matrix defining a 3D geometric form of the respective layer being casted,
    the method comprising:
        providing a 3D digital teeth model of the set of teeth in the patient's oral cavity comprising the one or more teeth to be reconstructed,
        generating an ordered set of 3D digital layer-specific molding matrices with each of the 3D digital layer-specific molding matrices being a negative of a 3D digital layer-specific reconstruction model of a set of 3D digital layer-specific reconstruction models, each of the 3D digital layer-specific reconstruction models according to the order adding another one of the layers to be reconstructed to the 3D digital teeth model,
        providing the ordered set of 3D digital layer-specific molding matrices as a set of templates for manufacturing the set of layer-specific molding matrices.
2. The method of claim 1, further comprising generating using the 3D digital teeth model the ordered set of 3D digital layer-specific reconstruction models, the ordered set of 3D digital layer-specific reconstruction models being used for generating the ordered set of 3D digital layer-specific molding matrices.
3. The method of feature combination 1, further comprising manufacturing the set of layer-specific molding matrices using the ordered set of 3D digital layer-specific molding matrices as templates, each of the manufactured layer-specific molding matrices of the set of layer-specific molding matrices being a physical copy of one of the templates.
4. The method of feature combination 2, the set of layer-specific molding matrices being manufactured using at least one of the following: machining, 3D printing, casting.
5. The method of any of the preceding feature combinations, the set of layer-specific molding matrices comprising two layer-specific molding matrices.
6. The method of any of the feature combinations 1 to 3, the set of layer-specific molding matrices comprising three layer-specific molding matrices.
7. The method of any of the preceding feature combinations, the set of layer-specific molding matrices comprising layer-specific molding matrices configured for casting one or more of the following types of layers: an oral enamel layer, a vestibular enamel layer, an oral dentin layer, a vestibular dentin layer.
8. The method of any of the preceding feature combinations, thicknesses of the layers added by the 3D digital layer-specific reconstruction models depending on at least one of the following: a target color of the one or more teeth to be reconstructed, target degrees of transparency of the reconstructed layers of the one or more teeth to be reconstructed, a target form of the one or more teeth to be reconstructed, minimum thickness required by the layer-specific reconstruction material intended to be used for reconstructing the respective layer.
9. The method of any of the preceding feature combinations, the layer-specific molding matrices comprising one or more injection channels configured for inserting the layer-specific reconstruction material by injecting the layer-specific reconstruction material into the layer-specific molding matrices.
10. The method of any of the preceding feature combinations, the layer-specific molding matrices comprising one or more venting channels configured for letting out air, when the layer-specific reconstruction material is inserted by injecting the layer-specific reconstruction material into the layer-specific molding matrices.
11. The method of any of the preceding feature combinations, the method further comprising:
    generating at least one 3D digital model of a mantle shell for at least one of the 3D digital layer-specific molding matrices, the 3D digital model of the mantle shell comprising a reception being a negative of an outer 3D geometrical form of the respective 3D digital layer-specific molding matrix, the 3D digital model of the mantle shell being configured to be slipped over the respective 3D digital layer-specific molding matrix arranged on one of the 3D digital layer-specific reconstruction models and providing structural support to the respective 3D digital layer-specific molding matrix, providing the at least one 3D digital model of the mantle shell as a template for manufacturing a physical copy of the 3D digital model of the mantle shell using the 3D digital model of the mantle shell as a template.

12. The method of feature combination 10, the reception comprising straight internal side-faces, the respective 3D digital layer-specific molding matrix comprising straight external side-faces in contact with the straight internal side-faces of the mantle shell, when the mantle shell is slipped over the respective layer-specific molding matrix.

13. The method of feature combination 11, the reception of the at least one 3D digital model of the mantle shell comprising a U-shaped cross section, the outer 3D geometrical form of the respective 3D digital layer-specific molding matrix comprising a U-shaped cross section in contact with the straight internal side-faces of the mantle shell, when the mantle shell is slipped over the respective layer-specific molding matrix.

14. The method of any of the feature combinations 10 to 12, further comprising manufacturing the physical copy of the at least one 3D digital model of the mantle shell using the at least one 3D digital model of the mantle shell as a template.

15. The method of feature combination 13, the physical copy of the at least one 3D digital model of the mantle shell being manufactured using at least one of the following: machining, 3D printing, casting.

16. The method of any of the feature combinations 13 to 14, the physical copy of the at least one 3D digital model of the mantle shell being manufactured using a material which is more rigid than a material used for manufacturing the layer-specific molding matrices.

17. The method of any of the feature combinations 10 to 15, the 3D digital model of the mantle shell comprising one or more injection channels configured for inserting the layer-specific reconstruction material by injecting the layer-specific reconstruction material into the layer-specific molding matrix, over which the 3D digital model of the mantle shell is slipped.

18. The method of any of the feature combinations 10 to 16, the 3D digital model of the mantle shell comprising one or more venting channels configured for letting out air, when the layer-specific reconstruction material is inserted by injecting the layer-specific reconstruction material into the layer-specific molding matrix, over which the 3D digital model of the mantle shell is slipped.

19. The method of any of the feature combinations 10 to 17, an individual 3D digital model of the mantle shell being generated and provided for each of the 3D digital layer-specific molding matrices of the ordered set of 3D digital layer-specific molding matrices.

20. The method of any of the feature combinations 10 to 19, a single common 3D digital model of the mantle shell being generated and provided for all the 3D digital layer-specific molding matrices of the ordered set of 3D digital layer-specific molding matrices.

21. The method of any of the preceding feature combinations, further comprising using a first trained machine learning module for generating the 3D digital layer-specific molding matrices of the ordered set of 3D digital layer-specific molding matrices, the first trained machine learning module being configured to provide the 3D digital layer-specific molding matrices as output in response to receiving the 3D digital teeth model as input.

22. The method of claim 21, further comprising providing the first trained machine learning module, the providing of the first trained machine learning module comprising:

providing a first machine learning module to be trained, providing a set of first training datasets for training the first machine learning module to be trained, each first training dataset comprising a first 3D digital training teeth model and an ordered set of 3D digital layer-specific training molding matrices, training the first machine learning module to be trained to provide the 3D digital layer-specific training molding matrices of the ordered set of 3D digital layer-specific training molding matrices of the first training datasets as output in response to receiving the first 3D digital training teeth models of the respective first training datasets as input.

23. The method of any of the feature combinations 2 to 20, further comprising using a second trained machine learning module for generating the 3D digital layer-specific reconstruction models of the ordered set of 3D digital layer-specific reconstruction models, the second trained machine learning module being configured to provide the 3D digital layer-specific reconstruction models as output in response to receiving the 3D digital teeth model as input.

24. The method of feature combination 23, further comprising providing the second trained machine learning module, the providing of the second trained machine learning module comprising:

providing a second machine learning module to be trained, providing a set of second training datasets for training the second machine learning module to be trained, each second training dataset comprising a second 3D digital training teeth model and an ordered set of 3D digital layer-specific training reconstruction models, training the second machine learning module to be trained to provide the 3D digital layer-specific training reconstruction models of the ordered set of 3D digital layer-specific training reconstruction models of the second training datasets as output in response to receiving the second 3D digital training teeth models of the respective second training datasets as input.

25. The method of any of the preceding feature combinations, the set of teeth comprising teeth of at least one of the following: a mandibular dental arch, a maxillary dental arch.

26. The method of any of the preceding feature combinations, the set of teeth being a set of natural teeth.

27. The method of any of the preceding feature combinations, the set of teeth comprising one or more artificial teeth.

28. A computer program product for providing a set of layer-specific molding matrices for reconstructing layer-by-layer one or more teeth of a set of teeth in a patient's oral cavity, the set of layer-specific molding matrices comprising two or more layer-specific molding matrices, each of the layer-specific molding matrices being configured for being arranged on the set of teeth and for casting a different layer of the one or more teeth to be reconstructed with a layer-specific reconstruction material inserted into the respective layer-specific molding matrix with the respective layer-specific molding matrix defining a 3D geometric form of the respective layer being casted, the computer program product comprising a computer readable storage medium having program instructions embodied therewith, the program instructions being executable by a processor of a computer device to cause the computer device to:

provide a 3D digital teeth model of the set of teeth in the patient's oral cavity comprising the one or more teeth to be reconstructed, generate using the 3D digital teeth model an ordered set of 3D digital layer-specific reconstruction models, each of the 3D digital layer-specific reconstruction models according to the order adding another one of the layers to be reconstructed to the 3D digital teeth model, generate using the ordered set of 3D digital layer-specific reconstruction models an ordered set of 3D digital layer-specific molding matrices with each of the 3D digital layer-specific molding matrices being a negative of one of the 3D digital layer-specific reconstruction models, provide the ordered set of 3D digital layer-specific molding matrices as a set of templates for manufacturing the set of layer-specific molding matrices.

29. A computer device for providing a set of layer-specific molding matrices for reconstructing layer-by-layer one or more teeth of a set of teeth in a patient's oral cavity, the set of layer-specific molding matrices comprising two or more layer-specific molding matrices, each of the layer-specific molding matrices being configured for being arranged on the set of teeth and for casting a different layer of the one or more teeth to be reconstructed with a layer-specific reconstruction material inserted into the respective layer-specific molding matrix with the respective layer-specific molding matrix defining a 3D geometric form of the respective layer being casted, the computer device comprising a processor and a memory storing program instructions executable by the processor, execution of the program instructions by the processor causing the computer device to:

provide a 3D digital teeth model of the set of teeth in the patient's oral cavity comprising the one or more teeth to be reconstructed, generate using the 3D digital teeth model an ordered set of 3D digital layer-specific reconstruction models, each of the 3D digital layer-specific reconstruction models according to the order adding another one of the layers to be reconstructed to the 3D digital teeth model, generate using the ordered set of 3D digital layer-specific reconstruction models an ordered set of 3D digital layer-specific molding matrices with each of the 3D digital layer-specific molding matrices being a negative of one of the 3D digital layer-specific reconstruction models, provide the ordered set of 3D digital layer-specific molding matrices as a set of templates for manufacturing the set of layer-specific molding matrices.

30. A manufacturing system comprising the computer device of feature combination 229, the manufacturing system further comprising a manufacturing device configured to manufacture the set of layer-specific molding matrices, execution of the program instructions by the processor further causing the computer device to control the manufacturing device to manufacture the set of layer-specific molding matrices using the ordered set of 3D digital layer-specific molding matrices as templates, each of the manufactured layer-specific molding matrices of the set of layer-specific molding matrices being a physical copy of one of the templates.

31. The manufacturing system of feature combination 29 to 30, the manufacturing device being one of the following: a machining device, a 3D printing device.

32. A set of layer-specific molding matrices for reconstructing layer-by-layer one or more teeth of a set of teeth in a patient's oral cavity, the set of layer-specific molding matrices comprising two or more layer-specific molding matrices, each of the layer-specific molding matrices being configured for being arranged on the set of teeth and for casting a different layer of the one or more teeth to be reconstructed with a layer-specific reconstruction material inserted into the respective layer-specific molding matrix with the respective layer-specific molding matrix defining a 3D geometric form of the respective layer being casted.

LIST OF REFERENCE NUMERALS 10 computer device
11 manufacturing system
14 external device
16 processing unit
18 bus
20 network adapter
22 I/O interface
24 display
28 memory
30 RAM
32 cache
34 storage system
40 program
42 program module
50 user interface
52 control elements
54 hardware device
56 keyboard
58 mouse
59 scanner
60 3D printing device
62 printing element
70 machining device
72 machining tool
74 holding device
76 blank
78 raw material
100 3D digital layer-specific molding matrix
101 layer-specific molding matrix
102 recess
104 injection channel
105 venting channel
106 recess
110 3D digital layer-specific molding matrix
111 layer-specific molding matrix
112 recess
114 injection channel 116 recess
120 3D digital layer-specific molding matrix
122 recess
124 injection channel
126 recess
130 tooth
132 reconstructed palatal enamel layer
134 reconstructed labial dentin layer
136 reconstructed labial enamel layer
140 mantle shell
142 sectional plane
144 reception
146 injection channel
148 venting channel
150 injection device
152 reconstruction material
160 3D digital layer-specific molding matrix
161 3D digital layer-specific molding matrix
162 recess
163 holding extension
164 injection channel
165 3D digital holding splint
166 recess
170 3D digital tooth model
172 tooth to be reconstructed

The invention claimed is:

1. A computer-implemented method for providing a set of layer-specific molding matrices for reconstructing layer-by-layer one or more teeth of a set of teeth in a patient's oral cavity, the set of layer-specific molding matrices comprising two or more layer-specific molding matrices, each of the layer-specific molding matrices being configured for being arranged on the set of teeth and for casting a different layer of the one or more teeth to be reconstructed with a layer-specific reconstruction material inserted into the respective layer-specific molding matrix with the respective layer-specific molding matrix defining a 3D geometric form of the respective layer being casted, the method comprising:
providing a 3D digital teeth model of the set of teeth in the patient's oral cavity comprising the one or more teeth to be reconstructed,
generating an ordered set of 3D digital layer-specific molding matrices with each of the 3D digital layer-specific molding matrices being a negative of a 3D digital layer-specific reconstruction model of a set of 3D digital layer-specific reconstruction models, each of the 3D digital layer-specific reconstruction models according to the order adding another one of the layers to be reconstructed to the 3D digital teeth model,
providing the ordered set of 3D digital layer-specific molding matrices as a set of templates for manufacturing the set of layer-specific molding matrices.

2. The method of claim 1, further comprising generating using the 3D digital teeth model the ordered set of 3D digital layer-specific reconstruction models, the ordered set of 3D digital layer-specific reconstruction models being used for generating the ordered set of 3D digital layer-specific molding matrices.

3. The method of claim 1, further comprising manufacturing the set of layer-specific molding matrices using the ordered set of 3D digital layer-specific molding matrices as templates, each of the manufactured layer-specific molding matrices of the set of layer-specific molding matrices being a physical copy of one of the templates.

4. The method of claim 3, the set of layer-specific molding matrices being manufactured using at least one of the following: machining, 3D printing, casting.

5. The method of claim 1, the set of layer-specific molding matrices comprising two layer-specific molding matrices.

6. The method of claim 1, the set of layer-specific molding matrices comprising three layer-specific molding matrices.

7. The method of claim 1, the set of layer-specific molding matrices comprising layer-specific molding matrices configured for casting one or more of the following types of layers: an oral enamel layer, a vestibular enamel layer, an oral dentin layer, a vestibular dentin layer.

8. The method of claim 1, thicknesses of the layers added by the 3D digital layer-specific reconstruction models depending on at least one of the following: a target color of the one or more teeth to be reconstructed, target degrees of transparency of the reconstructed layers of the one or more teeth to be reconstructed, a target form of the one or more teeth to be reconstructed, minimum thickness required by the layer-specific reconstruction material intended to be used for reconstructing the respective layer.

9. The method of claim 1, the layer-specific molding matrices comprising one or more injection channels configured for inserting the layer-specific reconstruction material by injecting the layer-specific reconstruction material into the layer-specific molding matrices.

10. The method of claim 1, the layer-specific molding matrices comprising one or more venting channels configured for letting out air, when the layer-specific reconstruction material is inserted by injecting the layer-specific reconstruction material into the layer-specific molding matrices.

11. The method of claim 1, the method further comprising:
generating at least one 3D digital model of a mantle shell for at least one of the 3D digital layer-specific molding matrices, the 3D digital model of the mantle shell comprising a reception being a negative of an outer 3D geometrical form of the respective 3D digital layer-specific molding matrix, the 3D digital model of the mantle shell being configured to be slipped over the respective 3D digital layer-specific molding matrix arranged on one of the 3D digital layer-specific reconstruction models and providing structural support to the respective 3D digital layer-specific molding matrix,
providing the at least one 3D digital model of the mantle shell as a template for manufacturing a physical copy of the 3D digital model of the mantle shell using the 3D digital model of the mantle shell as a template.

12. The method of claim 11, the reception comprising straight internal side-faces, the respective 3D digital layer-specific molding matrix comprising straight external side-faces in contact with the straight internal side-faces of the mantle shell, when the mantle shell is slipped over the respective layer-specific molding matrix.

13. The method of claim 12, the reception of the at least one 3D digital model of the mantle shell comprising a U-shaped cross section, the outer 3D geometrical form of the respective 3D digital layer-specific molding matrix comprising a U-shaped cross section in contact with the straight internal side-faces of the mantle shell, when the mantle shell is slipped over the respective layer-specific molding matrix.

14. The method of claim 11, further comprising manufacturing the physical copy of the at least one 3D digital model of the mantle shell using the at least one 3D digital model of the mantle shell as a template.

15. The method of claim 14, the physical copy of the at least one 3D digital model of the mantle shell being manufactured using at least one of the following: machining, 3D printing, casting.

16. The method of claim 14, the physical copy of the at least one 3D digital model of the mantle shell being manufactured using a material which is more rigid than a material used for manufacturing the layer-specific molding matrices.

17. The method of claim 11, the 3D digital model of the mantle shell comprising one or more injection channels configured for inserting the layer-specific reconstruction material by injecting the layer-specific reconstruction material into the layer-specific molding matrix, over which the 3D digital model of the mantle shell is slipped.

18. The method of claim 11, the 3D digital model of the mantle shell comprising one or more venting channels configured for letting out air, when the layer-specific reconstruction material is inserted by injecting the layer-specific reconstruction material into the layer-specific molding matrix, over which the 3D digital model of the mantle shell is slipped.

19. The method of claim 11, an individual 3D digital model of the mantle shell being generated and provided for each of the 3D digital layer-specific molding matrices of the ordered set of 3D digital layer-specific molding matrices.

20. The method of claim 11, a single common 3D digital model of the mantle shell being generated and provided for all the 3D digital layer-specific molding matrices of the ordered set of 3D digital layer-specific molding matrices.

21. The method of claim 1, further comprising using a first trained machine learning module for generating the 3D digital layer-specific molding matrices of the ordered set of 3D digital layer-specific molding matrices,
the first trained machine learning module being configured to provide the 3D digital layer-specific molding matrices as output in response to receiving the 3D digital teeth model as input.

22. The method of claim 21, further comprising providing the first trained machine learning module, the providing of the first trained machine learning module comprising:
providing a first machine learning module to be trained,
providing a set of first training datasets for training the first machine learning module to be trained, each first training dataset comprising a first 3D digital training teeth model and an ordered set of 3D digital layer-specific training molding matrices,
training the first machine learning module to be trained to provide the 3D digital layer-specific training molding matrices of the ordered set of 3D digital layer-specific training molding matrices of the first training datasets as output in response to receiving the first 3D digital training teeth models of the respective first training datasets as input.

23. The method of claim 1, further comprising using a second trained machine learning module for generating the 3D digital layer-specific reconstruction models of the ordered set of 3D digital layer-specific reconstruction models,
the second trained machine learning module being configured to provide the 3D digital layer-specific reconstruction models as output in response to receiving the 3D digital teeth model as input.

24. The method of claim 23, further comprising providing the second trained machine learning module, the providing of the second trained machine learning module comprising:
providing a second machine learning module to be trained,
providing a set of second training datasets for training the second machine learning module to be trained, each second training dataset comprising a second 3D digital training teeth model and an ordered set of 3D digital layer-specific training reconstruction models,
training the second machine learning module to be trained to provide the 3D digital layer-specific training reconstruction models of the ordered set of 3D digital layer-specific training reconstruction models of the second training datasets as output in response to receiving the second 3D digital training teeth models of the respective second training datasets as input.

25. The method of claim 1, the set of teeth comprising teeth of at least one of the following: a mandibular dental arch, a maxillary dental arch.

26. The method of claim 1, the set of teeth being a set of natural teeth.

27. The method of claim 1, the set of teeth comprising one or more artificial teeth.

28. A computer program product for providing a set of layer-specific molding matrices for reconstructing layer-by-layer one or more teeth of a set of teeth in a patient's oral cavity, the set of layer-specific molding matrices comprising two or more layer-specific molding matrices, each of the layer-specific molding matrices being configured for being arranged on the set of teeth and for casting a different layer of the one or more teeth to be reconstructed with a layer-specific reconstruction material inserted into the respective layer-specific molding matrix with the respective layer-specific molding matrix defining a 3D geometric form of the respective layer being casted,
the computer program product comprising a computer readable storage medium having program instructions embodied therewith, the program instructions being executable by a processor of a computer device to cause the computer device to:
provide a 3D digital teeth model of the set of teeth in the patient's oral cavity comprising the one or more teeth to be reconstructed,
generate an ordered set of 3D digital layer-specific molding matrices with each of the 3D digital layer-specific molding matrices being a negative of a 3D digital layer-specific reconstruction model of a set of 3D digital layer-specific reconstruction models, each of the 3D digital layer-specific reconstruction models according to the order adding another one of the layers to be reconstructed to the 3D digital teeth model,
provide the ordered set of 3D digital layer-specific molding matrices as a set of templates for manufacturing the set of layer-specific molding matrices.

29. A computer device for providing a set of layer-specific molding matrices for reconstructing layer-by-layer one or more teeth of a set of teeth in a patient's oral cavity, the set of layer-specific molding matrices comprising two or more layer-specific molding matrices, each of the layer-specific molding matrices being configured for being arranged on the set of teeth and for casting a different layer of the one or more teeth to be reconstructed with a layer-specific reconstruction material inserted into the respective layer-specific molding matrix with the respective layer-specific molding matrix defining a 3D geometric form of the respective layer being casted,
the computer device comprising a processor and a memory storing program instructions executable by the processor, execution of the program instructions by the processor causing the computer device to:

provide a 3D digital teeth model of the set of teeth in the patient's oral cavity comprising the one or more teeth to be reconstructed, generate an ordered set of 3D digital layer-specific molding matrices with each of the 3D digital layer-specific molding matrices being a negative of a 3D digital layer-specific reconstruction model of a set of 3D digital layer-specific reconstruction models, each of the 3D digital layer-specific reconstruction models according to the order adding another one of the layers to be reconstructed to the 3D digital teeth model, provide the ordered set of 3D digital layer-specific molding matrices as a set of templates for manufacturing the set of layer-specific molding matrices.

30. A manufacturing system comprising the computer device of claim 29, the manufacturing system further comprising a manufacturing device configured to manufacture the set of layer-specific molding matrices, execution of the program instructions by the processor further causing the computer device to control the manufacturing device to manufacture the set of layer-specific molding matrices using the ordered set of 3D digital layer-specific molding matrices as templates, each of the manufactured layer-specific molding matrices of the set of layer-specific molding matrices being a physical copy of one of the templates.

31. The manufacturing system of claim 30, the manufacturing device being one of the following: a machining device, a 3D printing device.

* * * * *